US006858597B2

(12) United States Patent
Reed et al.

(10) Patent No.: US 6,858,597 B2
(45) Date of Patent: Feb. 22, 2005

(54) HALOGENATED SULPHAMATE-, PHOSPHONATE-, THIOPHOSPHONATE-, SULPHONATE- AND SULPHONAMIDE- COMPOUNDS AS INHIBITORS OF STEROID SULPHATASE

(75) Inventors: Michael John Reed, The Oxford Science Park (GB); Barry Victor Lloyd Potter, The Oxford Science Park (GB); Hatem Hejaz, The Oxford Science Park (GB); Atul Purohit, The Oxford Science Park (GB)

(73) Assignee: Sterix Limited, Oxford (GB)

( * ) Notice: Subject to any disclaimer, the term of this patent is extended or adjusted under 35 U.S.C. 154(b) by 0 days.

(21) Appl. No.: 10/165,599

(22) Filed: Jun. 7, 2002

(65) Prior Publication Data

US 2003/0134829 A1 Jul. 17, 2003

(Under 37 CFR 1.47)

Related U.S. Application Data

(63) Continuation-in-part of application No. PCT/GB00/04689, filed on Dec. 7, 2000.

(30) Foreign Application Priority Data

| Dec. 13, 1999 | (GB) | ................................ 9929445 |
| Feb. 23, 2000 | (GB) | ................................ 0004317 |
| Jul. 21, 2000 | (GB) | ................................ 0018040 |

(51) Int. Cl.$^7$ ............................. A61K 31/56; C07J 1/00
(52) U.S. Cl. ........................................ 514/178; 552/626
(58) Field of Search ........................... 552/626; 514/178

(56) References Cited

U.S. PATENT DOCUMENTS 5,604,215 A 2/1997 Reed et al.

FOREIGN PATENT DOCUMENTS

| DE | 24 18 217 | 11/1975 |
| WO | WO93/05063 | 3/1993 |
| WO | WO93/05064 | 3/1993 |
| WO | WO98/24802 | 6/1998 |
| WO | WO 98/42729 | * 10/1998 |
| WO | WO99/27936 | 6/1999 |

OTHER PUBLICATIONS

Purohit et al., "The Development of A–Ring Modified Analogues of Oestrone–3–0–Sulphamate as Potent Steroid Sulphatase Inhibitors with Reduced Oestrogenicity", Journal of Steroid Biochem . . . , vol. 64, no 5, pp. 269–275, 1998 (XP000852539).

Woo et al., "Heteroatom–substituted analogues of the active–site directed inhibitor estra–1,3, 5(10)–trein–17–one–3–sulphamate inhibit estrone sulphatase by a different mechanism", Journal of Steroid Biochem . . . , vol 57 no 1–2, pp. 79–88, 1996 (XP002164108) Abstract.

Purohit et al., "Inhibition of steroid sulphatase activity by steroidal methylthiophosphonates: Potential therapeutic agents in breast cancer", Journal of Steroid Biochem., vol 48 no 5–6, pp. 523–527, 1994 (XP002164109) Abstract.

Howart et al., "PHosphonates and thiophosphonates as sulfate surrogates: Synthesis of estrone 3–methylthiophosphonate, a potent inhibitor of estrone sulfatase.", Bioorganic & Medicinal , vol. 3, No. 2 pp. 313–318, 1993 (XP002164110) Abstract.

Townsley J.D., "Furhter, Studies on the Regulation of Human Placental Steroid 3–Sulfatase Activity", Endocrinology, vol. 93, No. 1, pp. 172–181, 1973 (XP002068155).

Horwitz et al., "In vitro inhibition of estrogen sulfoconjugation by some 2– and 4– substituted estra–1, 3, 5(10)–trein–17.beta.–ols", J. Med. Chem., vol. 29, pp. 692–698, 1986 (XP002164107).

* cited by examiner

*Primary Examiner*—Barbara P. Badio
(74) *Attorney, Agent, or Firm*—Frommer Lawrence E Haug LLP; Thomas J. Kowalski

(57) ABSTRACT

A compound is described. The compound has the formula (Ia) as presented in the FIG. 1; wherein: X is a ring having at least 4 atoms in the ring; K is hydrocarbyl group; Rh1 is an optional halo group; Rh2 is an optional halo group; at least one of Rh1 and Rh2 is present; Rs is any one of a sulphamate group, a phosphonate group, a thiophosphonate group, a sulphonate group or a sulphonamide group. The compound is capable of inhibiting steroid sulphatase (STS) activity.

25 Claims, 10 Drawing Sheets

Figure 1A:
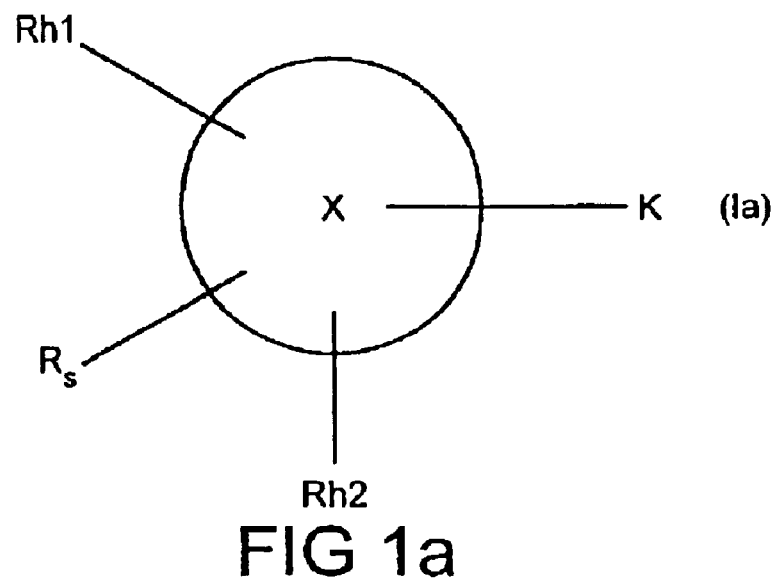

Scheme 1: Synthesis of 2-Bromo and 2-Iodooestrone-3-O-sulphamates.

Scheme 2: Synthesis of 2-FluoroEMATE

| Mean % Inhibition | SD % Inhibition | Treatments |
|---|---|---|
| 99.6 | 0.1 | 2SBH29F1 (2-BromoEMATE) 10µM |
| 98.8 | 0.1 | 2SBH29F1 (2-BromoEMATE) 1µM |
| 94.5 | 0.2 | 2SBH29F1 (2-BromoEMATE) 0.1µM |
| 85.1 | 0.1 | 2SBH29F1 (2-BromoEMATE) 10nM |
| 72.1 | 0.2 | 2SBH29F1 (2-BromoEMATE) 1nM |
| 46.1 | 0.3 | 2SBH29F1 (2-BromoEMATE) 0.1nM |
| 32.2 | 0.5 | 2SBH29F1 (2-BromoEMATE) 10pM |
| 19.7 | 1.2 | 2SBH29F1 (2-BromoEMATE) 1pM |
| 6.1 | 1.2 | 2SBH29F1 (2-BromoEMATE) 0.1pM |
| -6.7 | 0.7 | 2SBH29F1 (2-BromoEMATE) 10fM |
| 98.8 | 0.1 | EMATE 10µM |
| 95.1 | 0.1 | EMATE 1µM |
| 74.4 | 1.1 | EMATE 0.1µM |
| 24.3 | 3.5 | EMATE 10nM |
| -0.9 | 1.2 | EMATE 1nM |

HALOGENATED SULPHAMATE-, PHOSPHONATE-, THIOPHOSPHONATE-, SULPHONATE- AND SULPHONAMIDE-COMPOUNDS AS INHIBITORS OF STEROID SULPHATASE

RELATED APPLICATIONS

This application is a Continuation-in-Part of PCT/GB00/04689, filed Dec. 7, 2000, designating the U.S., published Jun. 21, 2001 as WO 01/44268 and claiming priority from GB9929445.6 filed 13 Dec. 1999, GB0004317.4 filed 23 Feb. 2000, GB0018040.6 filed 21 Jul. 2000 and international patent application number PCT/GB00/04689 filed 7 Dec. 2000.

Reference is also made to the following documents issued to the applicants: U.S. Pat. Nos. 6,239,169, 6,187,766, 6,159,960, 6,083,978, 6,017,904, 6,011,024, 5,861,390, 5,830,886, 5,616,574, 5,891,620, RE36701, 5,281,587, 5,344,827 and 5,604,215; International Publications WO 0151055, WO 0144268, WO 0076487, WO 0066095, WO 9964013, WO 9927936, WO 9927935, WO 9824802, WO 9732872, WO 9730041, WO 9305064, and WO9305063; and European Patents EP 0928609, EP 0921130, EP 1099706, EP 1085876, EP 1051178, EP 1051177, EP 0982032, EP 0928609, EP 0885211, EP 0880514, EP 0641355, and EP 0602123.

All of the above-mentioned documents, applications and patents, as well as all documents cited herein and documents referenced or cited in documents cited herein, are hereby incorporated herein by reference.

FIELD OF INVENTION

The present invention relates to a compound.

In particular the present invention relates to a compound and to a pharmaceutical composition comprising the compound. The present invention also relates to the use of the compound or composition in therapy applications.

BACKGROUND TO THE INVENTION

Evidence suggests that oestrogens are the major mitogens involved in promoting the growth of tumours in endocrine-dependent tissues, such as the breast and endometrium. Although plasma oestrogen concentrations are similar in women with or without breast cancer, breast tumour oestrone and oestradiol levels are significantly higher than in normal breast tissue or blood. In situ synthesis of oestrogen is thought to make an important contribution to the high levels of oestrogens in tumours and therefore inhibitors, in particular specific inhibitors, of oestrogen biosynthesis are of potential value for the treatment of endocrine-dependent tumours.

Over the past two decades, there has been considerable interest in the development of inhibitors of the aromatase pathway—which converts the androgen precursor androstenedione to oestrone. However, there is now evidence that the oestrone sulphatase (E1-STS) pathway, i.e. the hydrolysis of oestrone sulphate to oestrone (E1S to E1), as opposed to the aromatase pathway, is the major source of oestrogen in breast tumours. This theory is supported by a modest reduction of plasma oestrogen concentration in postmenopausal women with breast cancer treated by aromatase inhibitors, such as aminoglutethimide and 4-hydroxyandrostenedione, and also by the fact that plasma E1S concentration in these aromatase inhibitor-treated patients remains relatively high. The long half-life of E1S in blood (10–12 h) compared with the unconjugated oestrogens (20 min) and high levels of steroid sulphatase activity in liver and, normal and malignant breast tissues, also lend support to this theory.

PCT/GB92/01587 teaches novel steroid sulphatase inhibitors and pharmaceutical compositions containing them for use in the treatment of oestrone dependent tumours, especially breast cancer. These steroid sulphatase inhibitors are sulphamate esters, such as N,N-dimethyl oestrone-3-sulphamate and, preferably, oestrone-3-sulphamate (otherwise known as "EMATE").

EMATE (2-methoxyoestrone-3-O-sulphamate)—which is an analogue of oestrone-3-O-sulphamate—has the following structure:

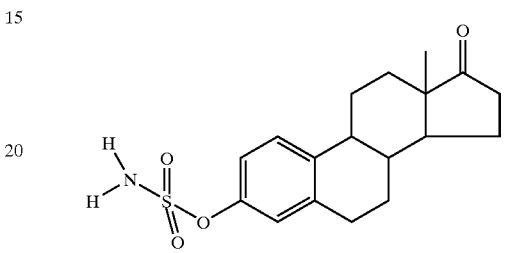

It is known that EMATE is a potent E1-STS inhibitor as it displays more than 99% inhibition of E1-STS activity in intact MCF-7 cells at 0.1 mM. EMATE also inhibits the E1-STS enzyme in a time- and concentration-dependent manner, indicating that it acts as an active site-directed inactivator. Although EMATE was originally designed for the inhibition of E1-STS, it also inhibits dehydroepiandrosterone sulphatase (DHA-STS), which is an enzyme that is believed to have a pivotal role in regulating the biosynthesis of the oestrogenic steroid androstenediol. Also, there is now evidence to suggest that androstenediol may be of even greater importance as a promoter of breast tumour growth. EMATE is also active in vivo as almost complete inhibition of rat liver E1-STS (99%) and DHA-STS (99%) activities resulted when it is administered either orally or subcutaneously. In addition, EMATE has been shown to have a memory enhancing effect in rats. Studies in mice have suggested an association between DHA-STS activity and the regulation of part of the immune response. It is thought that this may also occur in humans. The bridging O-atom of the sulphamate moiety in EMATE is important for inhibitory activity. Thus, when the 3-O-atom is replaced by other heteroatoms as in oestrone-3-N-sulphamate and oestrone-3-S-sulphamate, these analogues are weaker non-time-dependent inactivators.

Although optimal potency for inhibition of E1-STS may have been attained in EMATE, it is possible that oestrone may be released during sulphatase inhibition and that EMATE and its oestradiol congener may possess oestrogenic activity.

Ahmed et al (Biochem Biophys Res Commun 1999 Jan. 27;254(3):811–5) report on a structure-activity relationship study of steroidal and nonsteroidal inhibitors of STS.

The present invention seeks to provide novel compounds suitable for the inhibition of E1-STS as well as other therapeutic applications.

SUMMARY ASPECTS OF THE PRESENT INVENTION

The present invention is based on the surprising finding that certain halo-compounds could be used as effective steroid sulphatase inhibitors.

The halo compounds comprise at least one halo group that is a substituent of a ring system compound. The ring system compounds comprise at least one ring component. That ring component comprises at least 4 atoms in the ring. Typically, those 4 atoms will be carbon atoms. Thus, typically, that ring component will be a hydrocarbyl group. The ring system compound also includes one or more of a sulphamate group, a phosphonate group, a thiophosphonate group, a sulphonate group or a sulphonamide group as further substituent(s) on the ring system. At least one of the sulphamate group, the phosphonate group, the thiophosphonate group, the sulphonate group or the sulphonamide group is a substituent on the ring component. In a preferred aspect, the halo group(s) will be substituents on atom(s) that are adjacent the atom which bears the at least one sulphamate group, phosphonate group, thiophosphonate group, sulphonate group or sulphonamide group.

The halo compounds of the present invention may comprise other substituents. These other substituents may, for example, further increase the activity of the compounds of the present invention and/or increase stability (ex vivo and/or in vivo).

DETAILED ASPECTS OF THE PRESENT INVENTION

Figure 1B:
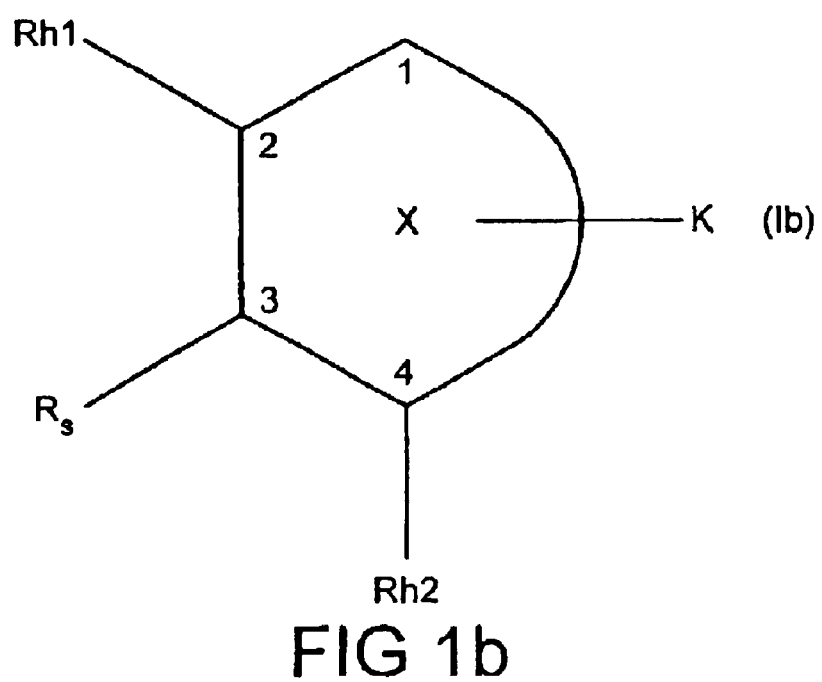

According to one aspect of the present invention, there is provided a compound of the formula (Ia) as presented in FIG. 1; wherein: X is a hydrocarbyl ring having at least 4 atoms in the ring; K is a hydrocarbyl group; Rh1 is an optional halo group; Rh2 is an optional halo group; at least one of Rh1 and Rh2 is present; Rs is any one of a sulphamate group, a phosphonate group, a thiophosphonate group, a sulphonate group or a sulphonamide group; and wherein said compound is capable of inhibiting steroid sulphatase (STS) activity.

According to one aspect of the present invention, there is provided a method comprising (a) performing a steroid sulphatase assay with one or more candidate compounds having the formula (Ia); (b) determining whether one or more of said candidate compounds is/are capable of modulating STS activity; and (c) selecting one or more of said candidate compounds that is/are capable of modulating STS activity.

According to one aspect of the present invention, there is provided a method comprising (a) performing a steroid sulphatase assay with one or more candidate compounds having the formula (Ia); (b) determining whether one or more of said candidate compounds is/are capable of inhibiting STS activity; and (c) selecting one or more of said candidate compounds that is/are capable of inhibiting STS activity.

In any one of the methods of the present invention, one or more additional steps may be present. For example, the method may also include the step of modifying the identified candidate compound (such as by chemical and/or enzymatic techniques) and the optional additional step of testing that modified compound for STS inhibition effects (which may be to see if the effect is greater or different). By way of further example, the method may also include the step of determining the structure (such as by use of crystallographic techniques) of the identified candidate compound and then performing computer modelling studies—such as to further increase its STS inhibitory action. Thus, the present invention also encompasses a computer having a dataset (such as the crystallographic co-ordinates) for said identified candidate compound. The present invention also encompasses that identified candidate compound when presented on a computer screen for the analysis thereof—such as protein binding studies.

According to one aspect of the present invention, there is provided a compound identified by the method of the present invention.

According to one aspect of the present invention, there is provided a compound according to the present invention for use in medicine.

According to one aspect of the present invention, there is provided a pharmaceutical composition comprising the compound according to the present invention optionally admixed with a pharmaceutically acceptable carrier, diluent, excipient or adjuvant.

According to one aspect of the present invention, there is provided the use of a compound according to the present invention in the manufacture of a medicament for use in the therapy of a condition or disease associated with STS.

According to one aspect of the present invention, there is provided the use of a compound according to the present invention in the manufacture of a medicament for use in the therapy of a condition or disease associated with adverse STS levels.

For ease of reference, these and further aspects of the present invention are now discussed under appropriate section headings. However, the teachings under each section are not necessarily limited to each particular section.

Preferable Aspects

Preferably, X in combination with Y mimics a steroidal structure.

Preferably, K is a cyclic group.

Preferably, X is a six-membered ring.

Preferably, the ring X has six carbon atoms in the ring.

Preferably, X in combination with Y is a steroidal ring structure.

Preferably, group K and ring X are a steroid ring structure or a substituted derivative thereof.

Preferably, the Rs group is at position 3 of the ring X.

Preferably, Rs is a sulphamate group.

Preferably, the Rh1 is at position 2 of the ring X.

Preferably, the Rh2 is at position 4 of the ring X.

Preferably, the compound of formula (Ia) has the formula presented as formula (Ib) wherein each of Rh1, Rh2, Rs, X and K have the above-mentioned meanings, and wherein at least one of Rh1 and Rh2 is present.

Preferably the group K and the ring X together will contain, inclusive of all substituents, a maximum of about 50 carbon atoms, more usually no more than about 30 to 40 carbon atoms.

For some applications, preferably the compounds have no, or a minimal, oestrogenic effect.

For some applications, preferably the compounds have an oestrogenic effect.

For some applications, preferably the compounds have a reversible action.

For some applications, preferably the compounds have an irreversible action.

In one embodiment, the compounds of the present invention are useful for the treatment of breast cancer.

Two preferred compounds are: 2-IodoEMATE and 2-BromoEMATE.

Some Advantages

One key advantage of the present invention is that the sulphamate compounds of the present invention can act as STS inhibitors.

Another advantage of the compounds of the present invention is that they may be potent in vivo.

Some of the compounds of the present invention may be non-oestrogenic compounds. Here, the term "non-oestrogenic" means exhibiting no or substantially no oestrogenic activity.

Another advantage is that some of the compounds may not be capable of being metabolised to compounds which display or induce hormonal activity.

Some of the compounds of the present invention are also advantageous in that they may be orally active.

Some of the compounds of the present invention may useful for the treatment of cancer, such as breast cancer, as well as (or in the alternative) non-malignant conditions, such as the prevention of auto-immune diseases, particularly when pharmaceuticals may need to be administered from an early age.

Thus, some of the compounds of the present invention are also believed to have to therapeutic uses other than for the treatment of endocrine-dependent cancers, such as the treatment of autoimmune diseases.

Steroid Sulphatase

Steroid sulphatase—which is sometimes referred to as steroid sulfatase or steryl sulphatase or "STS" for short—hydrolyses several sulphated steroids, such as oestrone sulphate, dehydroepiandrosterone sulphate and cholesterol sulphate. STS has been allocated the enzyme number EC 3.1.6.2.

STS has been cloned and expressed. For example see Stein et al (J. Biol. Chem. 264:13865–13872 (1989)) and Yen et al (Cell 49:443–454(1987)).

STS is an enzyme that has been implicated in a number of disease conditions.

By way of example, workers have found that a total deficiency in STS produces ichthyosis. According to some workers, STS deficiency is fairly prevalent in Japan. The same workers (Sakura et al, J Inherit Metab Dis 1997 November;20(6):807–10) have also reported that allergic diseases—such as bronchial asthma, allergic rhinitis, or atopic dermatitis—may be associated with a steroid sulphatase deficiency.

In addition to disease states being brought on through a total lack of STS activity, an increased level of STS activity may also bring about disease conditions. By way of example, and as indicated above, there is strong evidence to support a role of STS in breast cancer growth and metastasis.

STS has also been implicated in other disease conditions. By way of example, Le Roy et al (Behav Genet 1999 March;29(2):131–6) have determined that there may be a genetic correlation between steroid sulphatase concentration and initiation of attack behaviour in mice. The authors conclude that sulphatation of steroids may be the prime mover of a complex network, including genes shown to be implicated in aggression by mutagenesis.

STS Inhibition

It is believed that some disease conditions associated with STS activity are due to conversion of a nonactive, sulphated oestrone to an active, nonsulphated oestrone. In disease conditions associated with STS activity, it would be desirable to inhibit STS activity.

Here, the term "inhibit" includes reduce and/or eliminate and/or mask and/or prevent the detrimental action of STS.

STS Inhibitor

In accordance with the present invention, the compound of the present invention is capable of acting as an STS inhibitor.

Here, the term "inhibitor" as used herein with respect to the compound of the present invention means a compound that can inhibit STS activity—such as reduce and/or eliminate and/or mask and/or prevent the detrimental action of STS. The STS inhibitor may act as an antagonist.

The ability of compounds to inhibit oestrone sulphatase activity can be assessed using either intact MCF-7 breast cancer cells or placental microsomes. In addition, an animal model may be used. Details on suitable Assay Protocols are presented in following sections. It is to be noted that other assays could be used to determine STS activity and thus STS inhibition. For example, reference may also be made to the teachings of WO-A-99/50453.

Preferably, for some applications, the compound is further characterised by the feature that if the sulphamate group were to be substituted by a sulphate group to form a sulphate derivative, then the sulphate derivative would be hydrolysable by an enzyme having steroid sulphatase (E.C. 3.1.6.2) activity—i.e. when incubated with steroid sulphatase EC 3.1.6.2 at pH 7.4 and 37° C.

In one preferred embodiment, if the sulphamate group of the compound were to be replaced with a sulphate group to form a sulphate compound then that sulphate compound would be hydrolysable by an enzyme having steroid sulphatase (E.C. 3.1.6.2) activity and would yield a Km value of less than 200 mmolar, preferably less than 150 mmolar, preferably less than 100 mmolar, preferably less than 75 mmolar, preferably less than 50 mmolar, when incubated with steroid sulphatase EC 3.1.6.2 at pH 7.4 and 37° C.

In a preferred embodiment, the compound of the present invention is not hydrolysable by an enzyme having steroid sulphatase (E.C. 3.1.6.2) activity.

For some applications, preferably the compound of the present invention has at least about a 100 fold selectivity to a desired target (e.g. STS), preferably at least about a 150 fold selectivity to the desired target, preferably at least about a 200 fold selectivity to the desired target, preferably at least about a 250 fold selectivity to the desired target, preferably at least about a 300 fold selectivity to the desired target, preferably at least about a 350 fold selectivity to the desired target.

It is to be noted that the compound of the present invention may have other beneficial properties in addition to or in the alternative to its ability to inhibit STS activity.

Group K

Group K need not be a cyclic structure. In this regard, group K may be a linear structure that may have the ability to conform to a ring like structure when in in vivo.

In a preferred aspect, group K is cyclic—so as to form the cyclic group K.

Cyclic group K need not necessarily be fused to ring X. In this regard, they may be separated by a suitable spacer group—which may be a hydrocarbyl group.

In a preferred aspect, cyclic group K is fused to ring X.

Group K may be a polycyclic group, which need not be a fused polycycle.

Thus, in a preferred aspect, group K and ring X make up a polycyclic compound. As indicated, here the term "polycyclic" includes fused and non-fused ring structures including combinations thereof.

At least one of the cyclic groups K and X may be a heterocyclic group (a heterocycle) or a non-heterocyclic group.

At least one of the cyclic groups K and X may be a saturated ring structure or an unsaturated ring structure (such as an aryl group).

Preferably, at least one of the cyclic groups is an aryl ring.

If the cyclic group is polycyclic some or all of the ring components of the compound may be fused together or joined via one or more suitable spacer groups.

The polycyclic compound may comprise a number of fused rings. In this aspect the fused rings may comprise any combination of different size rings, such as 3 six-membered rings (6,6,6), a six-membered ring, a seven-membered ring and a six-membered ring (6,7,6), a six-membered ring and two eight-membered rings (6,8,8) etc.

In one aspect the present invention relates to compounds wherein the polycyclic compounds are other than (6,6,7) rings. In a further aspect, the present invention relates to compounds wherein the polycyclic compounds only contain rings having other than 7 members.

Preferably the polycyclic compound will contain, inclusive of all substituents, no more than 50 about carbon atoms, more usually no more than about 30 to 40 carbon atoms.

The polycyclic compound can comprise at least two ring components, or at least three ring components, or at least four ring components.

Preferably, the polycyclic compound comprises four ring components.

Preferred polycyclic compounds have a steroidal ring component, or bio-isosteres thereof.

Hydrocarbyl

The term "hydrocarbyl group" as used herein means a group comprising at least C and H and may optionally comprise one or more other suitable substituents. Examples of such substituents may include halo, alkoxy, nitro, an alkyl group, a cyclic group etc. In addition to the possibility of the substituents being a cyclic group, a combination of substituents may form a cyclic group. If the hydrocarbyl group comprises more than one C then those carbons need not necessarily be linked to each other. For example, at least two of the carbons may be linked via a suitable element or group. Thus, the hydrocarbyl group may contain hetero atoms. Suitable hetero atoms will be apparent to those skilled in the art and include, for instance, sulphur, nitrogen and oxygen. A non-limiting example of a hydrocarbyl group is an acyl group.

A typical hydrocarbyl group is a hydrocarbon group. Here the term "hydrocarbon" means any one of an alkyl group, an alkenyl group, an alkynyl group, which groups may be linear, branched or cyclic, or an aryl group. The term hydrocarbon also includes those groups but wherein they have been optionally substituted. If the hydrocarbon is a branched structure having substituent(s) thereon, then the substitution may be on either the hydrocarbon backbone or on the branch; alternatively the substitutions may be on the hydrocarbon backbone and on the branch.

Sulphamate Group

In one embodiment, the ring X has a sulphamate group as a substituent. The term "sulphamate" as used herein includes an ester of sulphamic acid, or an ester of an N-substituted derivative of sulphamic acid, or a salt thereof.

If Rs is a sulphamate group then the compound of the present invention is referred to as a sulphamate compound.

Typically, the sulphamate group has the formula:

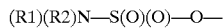
(R1)(R2)N—S(O)(O)—O— wherein preferably R1 and R2 are independently selected from H, alkyl, cycloalkyl, alkenyl and aryl, or combinations thereof, or together represent alkylene, wherein the or each alkyl or cycloalkyl or alkenyl or optionally contain one or more hetero atoms or groups.

When substituted, the N-substituted compounds of this invention may contain one or two N-alkyl, N-alkenyl, N-cycloalkyl or N-aryl substituents, preferably containing or each containing a maximum of 10 carbon atoms. When R1 and/or R2 is alkyl, the preferred values are those where R1 and R2 are each independently selected from lower alkyl groups containing from 1 to 6 carbon atoms, that is to say methyl, ethyl, propyl etc. R1 and R2 may both be methyl. When R1 and/or R2 is aryl, typical values are phenyl and tolyl (PhCH3; o). Where R1 and R2 represent cycloalkyl, typical values are cyclopropyl, cyclopentyl, cyclohexyl etc. When joined together R1 and R2 typically represent an alkylene group providing a chain of 4 to 6 carbon atoms, optionally interrupted by one or more hetero atoms or groups, e.g. to provide a 5 membered heterocycle, e.g. morpholino, pyrrolidino or piperidino.

Within the values alkyl, cycloalkyl, alkenyl and aryl substituted groups are included containing as substituents therein one or more groups which do not interfere with the sulphatase inhibitory activity of the compound in question. Exemplary non-interfering substituents include hydroxy, amino, halo, alkoxy, alkyl and aryl.

In some embodiments, the sulphamate group may form a ring structure by being fused to (or associated with) one or more atoms in or on group X.

In some embodiments, there may be more than one sulphamate group. By way of example, there may be two sulphamates (i.e. bis-sulphamate compounds). If these compounds are based on a steroidal nucleus, preferably the second (or at least one of the additional) sulphamate group is located at position 17 of the steroidal nucleus. These groups need not be the same.

In some preferred embodiments, at least one of R1 and R2 is H.

In some further preferred embodiments, each of R1 and R2 is H.

Phosphonate Group

If Rs is a phosphonate group then the compound of the present invention is referred to as a phosphonate compound.

Typically, the phosphonate group has the formula:

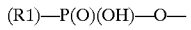
(R1)—P(O)(OH)—O— wherein preferably R1 is H, alkyl, cycloalkyl, alkenyl or aryl, or combinations thereof, wherein the or each alkyl or cycloalkyl or alkenyl or optionally contain one or more hetero atoms or groups.

When substituted, the N-substituted compounds of this invention may contain one or two N-alkyl, N-alkenyl, N-cycloalkyl or N-aryl substituents, preferably containing or each containing a maximum of 10 carbon atoms. When R1 is alkyl, R1 may be a lower alkyl groups containing from 1 to 6 carbon atoms, that is to say methyl, ethyl, propyl etc. By way of example, R1 may be methyl. When R1 is aryl, typical values are phenyl and tolyl (PhCH3;o). Where R1 represents cycloalkyl, typical values are cyclopropyl, cyclopentyl, cyclohexyl etc. R1 may even comprise an alkylene group providing a chain of 4 to 6 carbon atoms, optionally interrupted by one or more hetero atoms or groups, e.g. to provide a 5 membered heterocycle, e.g. morpholino, pyrrolidino or piperidino.

Within the values alkyl, cycloalkyl, alkenyl and aryl substituted groups are included containing as substituents therein one or more groups which do not interfere with the sulphatase inhibitory activity of the compound in question. Exemplary non-interfering substituents include hydroxy, amino, halo, alkoxy, alkyl and aryl.

In some embodiments, the phosphonate group may form a ring structure by being fused to (or associated with) one or more atoms in or on group X.

In some embodiments, there may be more than one phosphonate group. By way of example, there may be two phosphonates (i.e. bis-phosphonate compounds). If these compounds are based on a steroidal nucleus, preferably the second (or at least one of the additional) phosphonate group is located at position 17 of the steroidal nucleus. These groups need not be the same.

Thiophosphonate Group

If Rs is a thiophosphonate group then the compound of the present invention is referred to as a thiophosphonate compound.

Typically, the thiophosphonate group has the formula:

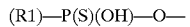

(R1)—P(S)(OH)—O— wherein preferably R1 is H, alkyl, cycloalkyl, alkenyl or aryl, or combinations thereof, wherein the or each alkyl or cycloalkyl or alkenyl or optionally contain one or more hetero atoms or groups.

When substituted, the N-substituted compounds of this invention may contain one or two N-alkyl, N-alkenyl, N-cycloalkyl or N-aryl substituents, preferably containing or each containing a maximum of 10 carbon atoms. When R1 is alkyl, R1 may be a lower alkyl groups containing from 1 to 6 carbon atoms, that is to say methyl, ethyl, propyl etc. By way of example, R1 may be methyl. When R1 is aryl, typical values are phenyl and tolyl (PhCH3;o). Where R1 represents cycloalkyl, typical values are cyclopropyl, cyclopentyl, cyclohexyl etc. R1 may even comprise an alkylene group providing a chain of 4 to 6 carbon atoms, optionally interrupted by one or more hetero atoms or groups, e.g. to provide a 5 membered heterocycle, e.g. morpholino, pyrrolidino or piperidino.

Within the values alkyl, cycloalkyl, alkenyl and aryl substituted groups are included containing as substituents therein one or more groups which do not interfere with the sulphatase inhibitory activity of the compound in question. Exemplary non-interfering substituents include hydroxy, amino, halo, alkoxy, alkyl and aryl.

In some embodiments, the thiophosphonate group may form a ring structure by being fused to (or associated with) one or more atoms in or on group X.

In some embodiments, there may be more than one thiophosphonate group. By way of example, there may be two thiophosphonates (i.e. bis-thiophosphonate compounds). If these compounds are based on a steroidal nucleus, preferably the second (or at least one of the additional) thiophosphonate group is located at position 17 of the steroidal nucleus. These groups need not be the same.

Sulphonate Group

If Rs is a sulphonate group then the compound of the present invention is referred to as a sulphonate compound.

Typically, the sulphonate group has the formula:

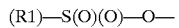

(R1)—S(O)(O)—O— wherein preferably R1 is H, alkyl, cycloalkyl, alkenyl or aryl, or combinations thereof, wherein the or each alkyl or cycloalkyl or alkenyl or optionally contain one or more hetero atoms or groups.

When substituted, the N-substituted compounds of this invention may contain one or two N-alkyl, N-alkenyl, N-cycloalkyl or N-aryl substituents, preferably containing or each containing a maximum of 10 carbon atoms. When R1 is alkyl, R1 may be a lower alkyl groups containing from 1 to 6 carbon atoms, that is to say methyl, ethyl, propyl etc. By way of example, R1 may be methyl. When R1 is aryl, typical values are phenyl and tolyl (PhCH3;o). Where R1 represents cycloalkyl, typical values are cyclopropyl, cyclopentyl, cyclohexyl etc. R1 may even comprise an alkylene group providing a chain of 4 to 6 carbon atoms, optionally interrupted by one or more hetero atoms or groups, e.g. to provide a 5 membered heterocycle, e.g. morpholino, pyrrolidino or piperidino.

Within the values alkyl, cycloalkyl, alkenyl and aryl substituted groups are included containing as substituents therein one or more groups which do not interfere with the sulphatase inhibitory activity of the compound in question. Exemplary non-interfering substituents include hydroxy, amino, halo, alkoxy, alkyl and aryl.

In some embodiments, the sulphonate group may form a ring structure by being fused to (or associated with) one or more atoms in or on group X.

In some embodiments, there may be more than one sulphonate group. By way of example, there may be two sulphonates (i.e. bis-sulphonate compounds). If these compounds are based on a steroidal nucleus, preferably the second (or at least one of the additional) sulphonate group is located at position 17 of the steroidal nucleus. These groups need not be the same.

Combination Sulphonate/Phosphonate/Thiophosphonate/Sulphamate

For some compounds of the present invention there may be present one of a sulphonate as herein defined or a phosphonate as herein defined or a thiophosphonate as herein defined or a sulphamate as herein defined; and another of a sulphonate as herein defined or a phosphonate as herein defined or a thiophosphonate as herein defined or a sulphamate as herein defined. By way of example, the compound of the present invention may comprise one sulphamate group and one phosphonate group.

If these compounds of the present invention are based on a steroidal nucleus, preferably the other of said groups is located at position 17 of the steroidal nucleus.

Mimic

In one aspect, X and K can be a mimic of a steroidal ring structure

The term "mimic" as used herein means having a similar or different structure but having a similar functional effect. In other words, group K and ring X together may be a bio-isostere of the rings of a steroid, or an active part thereof.

In a preferred aspect, group K and ring X together may be a bio-isostere of the rings of oestrone, or a part thereof.

Steroidal Ring Structure

In one preferred aspect, X and K make up a steroidal ring structure—that is to say a cyclopentanophenanthrene skeleton, or bio-isosteres thereof.

As it is well known in the art, a classical steroidal ring structure has the generic formula of:

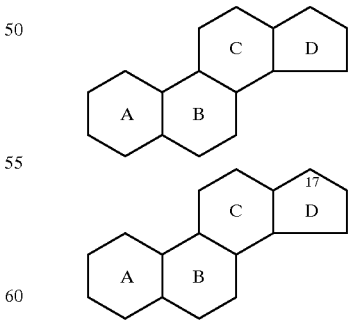

In the above formula, the rings have been labelled in the conventional manner.

An example of a bio-isostere is when any one or more of rings A, B, C and D is a heterocyclic ring and/or when any one or more of rings A, B, C and D has been substituted and/or when any one or more of rings A, B, C and D has been modified; but wherein the bio-isostere in the absence of the sulphamate group has steroidal properties.

In this regard, the structure of a preferred polycyclic structure can be presented as:

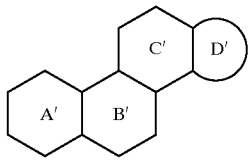

wherein each ring A', B', C' and D' independently represents a heterocyclic ring or a non-heterocyclic ring, which rings may be independently substituted or unsubstituted, saturated or unsaturated.

By way of example, any one or more of rings A', B', C' and D' may be independently substituted with suitable groups— such as an alkyl group, an aryl group, a hydroxy group, a halo group, a hydrocarbyl group, an oxyhydrocarbyl group etc.

An example of D' is a five or six membered non-heterocyclic ring having at least one substituent.

In one preferred embodiment, the ring D' is substituted with a ethinyl group.

If any one of rings A', B', C' and D' is a heterocyclic ring, then preferably that heterocyclic ring comprises a combination of C atoms and at least one N atom and/or at least one O atom. Other heterocyclic atoms may be present in the ring.

Examples of suitable, preferred steroidal nuclei rings A'–D' of the compounds of the present invention include rings A–D of dehydroepiandrosterone and oestrogens including oestrone.

Preferred steroidal nuclei rings A'–D' of the compounds of the present invention include rings A–D of:

Oestrones and Substituted Oestrones, viz:

oestrone
4-OH-oestrone
6α-OH-oestrone
7α-OH-oestrone
16α-OH-oestrone
16β-OH-oestrone
17-deoxyoestrone
oestrone Oestradiols and Substituted Oestradiols, viz:

4-OH-17β-oestradiol
6α-OH-17β-oestradiol
7α-OH-17β-oestradiol
4-OH-17α-oestradiol
6α-OH-17α-oestradiol
7α-OH-17α-oestradiol
16α-OH-17α-oestradiol
16α-OH-17β-oestradiol
16β-OH-17α-oestradiol
16β-OH-17β-oestradiol
17α-oestradiol
17β-oestradiol
17α-ethinyl-17β-oestradiol
17β-ethinyl-17α-oestradiol
17-deoxyoestradiol Oestriols and Substituted Oestriols, viz:

oestriol
4-OH-oestriol
6α-OH-oestriol
7α-OH-oestriol
17-deoxyoestriol

Dehydroepiandrosterones and Substituted Dehydroepiandrosterones, viz:

dehydroepiandrosterones
6α-OH-dehydroepiandrosterone
7α-OH-dehydroepiandrosterone
16α-OH-dehydroepiandrosterone
16β-OH-dehydroepiandrosterone In general terms the ring system A'B'C'D' may contain a variety of non-interfering substituents. In particular, the ring system A'B'C'D' may contain one or more hydroxy, alkyl especially lower ($C_1$–$C_6$) alkyl, e.g. methyl, ethyl, n-propyl, isopropyl, n-butyl, sec-butyl, tert-butyl, n-pentyl and other pentyl isomers, and n-hexyl and other hexyl isomers, alkoxy especially lower ($C_1$–$C_6$) alkoxy, e.g. methoxy, ethoxy, propoxy etc., alkinyl, e.g. ethinyl, or halogen, e.g. fluoro substituents.

Non-Steroid Structures

In an alternative embodiment, the compound of the present invention may not contain or be based on a steroid nucleus. In this regard, the polycyclic compound may contain or be based on a non-steroidal ring system—such as diethylstilboestrol, stilboestrol, coumarins, flavonoids, combrestatin and other ring systems. Other suitable non-steroidal compounds for use in or as the composition of the present invention may be found in U.S. Pat. No. 5,567,831.

Other Substituents

The compound of the present invention may have substituents other than Rh1, Rh2 and Rs. By way of example, these other substituents may be one or more of: one or more sulphamate group(s), one or more phosphonate group(s), one or more thiophosphonate group(s), one or more sulphonate group(s), one or more sulphonamide group(s), one or more halo groups, one or more O groups, one or more hydroxy groups, one or more amino groups, one or more sulphur containing group(s), one or more hydrocarbyl group(s)—such as an oxyhydrocarbyl group.

Oxyhydrocarbyl

The term "oxyhydrocarbyl" group as used herein means a group comprising at least C, H and O and may optionally comprise one or more other suitable substituents. Examples of such substituents may include halo-, alkoxy-, nitro-, an alkyl group, a cyclic group etc. In addition to the possibility of the substituents being a cyclic group, a combination of substituents may form a cyclic group. If the oxyhydrocarbyl group comprises more than one C then those carbons need not necessarily be linked to each other. For example, at least two of the carbons may be linked via a suitable element or group. Thus, the oxyhydrocarbyl group may contain hetero atoms. Suitable hetero atoms will be apparent to those skilled in the art and include, for instance, sulphur and nitrogen.

In one embodiment of the present invention, the oxyhydrocarbyl group is a oxyhydrocarbon group.

Here the term "oxyhydrocarbon" means any one of an alkoxy group, an oxyalkenyl group, an oxyalkynyl group, which groups may be linear, branched or cyclic, or an oxyaryl group. The term oxyhydrocarbon also includes those groups but wherein they have been optionally substituted. If the oxyhydrocarbon is a branched structure having substituent(s) thereon, then the substitution may be on either the hydrocarbon backbone or on the branch; alternatively the substitutions may be on the hydrocarbon backbone and on the branch.

Typically, the oxyhydrocarbyl group is of the formula $C_{1-6}O$ (such as a $C_{1-3}O$).

Assay for Determining STS Activity Using Cancer Cells (Protocol 1)

Inhibition of Steroid Sulphatase Activity in MCF-7 Cells

Steroid sulphatase activity is measured in vitro using intact MCF-7 human breast cancer cells. This hormone dependent cell line is widely used to study the control of human breast cancer cell growth. It possesses significant steroid sulphatase activity (MacIndoe et al. Endocrinology, 123, 1281–1287 (1988); Purohit & Reed, Int. J. Cancer, 50, 901–905 (1992)) and is available in the U.S.A. from the American Type Culture Collection (ATCC) and in the U.K. (e.g. from The Imperial Cancer Research Fund).

Cells are maintained in Minimal Essential Medium (MEM) (Flow Laboratories, Irvine, Scotland) containing 20 mM HEPES, 5% foetal bovine serum, 2 mM glutamine, non-essential amino acids and 0.075% sodium bicarbonate. Up to 30 replicate 25 cm2 tissue culture flasks are seeded with approximately $1 \times 10^5$ cells/flask using the above medium. Cells are grown to 80% confluency and the medium is changed every third day.

Intact monolayers of MCF-7 cells in triplicate 25 cm$^2$ tissue culture flasks are washed with Earle's Balanced Salt Solution (EBSS from ICN Flow, High Wycombe, U.K.) and incubated for 3–hours at 37° C. with 5 pmol ($7 \times 10^5$ dpm) [6,7-3H]oestrone-3-sulphate (specific activity 60 Ci/mmol from New England Nuclear, Boston, Mass., U.S.A.) in serum-free MEM (2.5 ml) together with oestrone-3-sulphamate (11 concentrations: 0; 1 fM; 0.01 pM; 0.1 pM; 1 pM; 0.01 mM; 0.1 mM; 1 mM; 0.01 mM; 0.1 mM; 1 mM). After incubatio each flask is cooled and the medium (1 ml) is pipetted into separate tubes containing [14C]oestrone ($7 \times 10^3$ dpm) (specific activity 97 Ci/mmol from Amersham International Radiochemical Centre, Amersham, U.K.). The mixture is shaken thoroughly for 30 seconds with toluene (5 ml). Experiments have shown that >90% [14C] oestrone and <0.1% [3H]oestrone-3-sulphate is removed from the aqueous phase by this treatment. A portion (2 ml) of the organic phase is removed, evaporated and the 3H and 14C content of the residue determined by scintillation spectrometry. The mass of oestrone-3-sulphate hydrolysed was calculated from the 3H counts obtained (corrected for the volumes of the medium and organic phase used, and for recovery of [14C] oestrone added) and the specific activity of the substrate. Each batch of experiments includes incubations of microsomes prepared from a sulphatase-positive human placenta (positive control) and flasks without cells (to assess apparent non-enzymatic hydrolysis of the substrate). The number of cell nuclei per flask is determined using a Coulter Counter after treating the cell monolayers with Zaponin. One flask in each batch is used to assess cell membrane status and viability using the Trypan Blue exclusion method (Phillips, H. J. (1973) In: Tissue culture and applications, [eds: Kruse, D. F. & Patterson, M. K.]; pp. 406–408; Academic Press, New York).

Results for steroid sulphatase activity are expressed as the mean±1 S.D. of the total product (oestrone+oestradiol) formed during the incubation period (20 hours) calculated for 106 cells and, for values showing statistical significance, as a percentage reduction (inhibition) over incubations containing no oestrone-3-sulphamate. Unpaired Student's t-test was used to test the statistical significance of results.

Assay for Determining STS Activity Using Placental Microsomes (Protocol 2)

Inhibition of Steroid Sulphatase Activity in Placental Microsomes

Sulphatase-positive human placenta from normal term pregnancies are thoroughly minced with scissors and washed once with cold phosphate buffer (pH 7.4, 50 mM) then re-suspended in cold phosphate buffer (5 ml/g tissue). Homogenisation is accomplished with an Ultra-Turrax homogeniser, using three 10 second bursts separated by 2 minute cooling periods in ice. Nuclei and cell debris are removed by centrifuging (4° C.) at 2000 g for 30 minutes and portions (2 ml) of the supernatant are stored at 20° C. The protein concentration of the supernatants is determined by the method of Bradford (Anal. Biochem., 72, 248–254 (1976)).

Incubations (1 ml) are carried out using a protein concentration of 100 mg/ml, substrate concentration of 20 mM [6,7-3H]oestrone-3-sulphate (specific activity 60 Ci/mmol from New England Nuclear, Boston, Mass., U.S.A.) and an incubation time of 20 minutes at 37° C. If necessary eight concentrations of compounds are employed: 0 (i.e. control); 0.05 mM; 0.1 mM; 0.2 mM; 0.4 mM; 0.6 mM; 0.8 mM; 1.0 mM. After incubation each sample is cooled and the medium (1 ml) was pipetted into separate tubes containing [14C] oestrone ($7 \times 103$ dpm) (specific activity 97 Ci/mmol from Amersham International Radiochemical Centre, Amersham, U.K.). The mixture is shaken thoroughly for 30 seconds with toluene (5 ml). Experiments have shown that >90% [14C] oestrone and <0.1% [3H]oestrone-3-sulphate is removed from the aqueous phase by this treatment. A portion (2 ml) of the organic phase was removed, evaporated and the 3H and 14C content of the residue determined by scintillation spectrometry. The mass of oestrone-3-sulphate hydrolysed is calculated from the 3H counts obtained (corrected for the volumes of the medium and organic phase used, and for recovery of [14C]oestrone added) and the specific activity of the substrate.

Animal Assay Model for Determining STS Activity (Protocol 3)

Inhibition of Oestrone Sulphatase Activity in vivo

The compounds of the present invention may be studied using an animal model, in particular in ovariectomised rats. In this model compounds which are oestrogenic stimulate uterine growth.

The compound (0.1 mg/Kg/day for five days) is administered orally to rats with another group of animals receiving vehicle only (propylene glycol). At the end of the study samples of liver tissue were obtained and oestrone sulphatase activity assayed using 3H oestrone sulphate as the substrate as previously described (see PCT/GB95/02638).

Animal Assay Model for Determining Oestrogenic Activity (Protocol 4)

Lack of in vivo Oestrogenicity

The compounds of the present invention may be studied using an animal model, in particular in ovariectomised rats. In this model, compounds which are oestrogenic stimulate uterine growth.

The compound (0.1 mg/Kg/day for five days) was administered orally to rats with another group of animals receiving vehicle only (propylene glycol). At the end of the study uteri were obtained and weighed with the results being expressed as uterine weight/whole body weight×100.

Compounds having no significant effect on uterine growth are not oestrogenic.

Biotechnological Assays for Determining STS Activity (Protocol 5)

The ability of compounds to inhibit oestrone sulphatase activity can also be assessed using amino acid sequences or nucleotide sequences encoding STS, or active fragments, derivatives, homologues or variants thereof in, for example, high-through put screens.

Any one or more of appropriate targets—such as an amino acid sequence and/or nucleotide sequence—may be used for identifying an agent capable of modulating STS in any of a variety of drug screening techniques. The target employed in such a test may be free in solution, affixed to a solid support, borne on a cell surface, or located intracellularly. The abolition of target activity or the formation of binding complexes between the target and the agent being tested may be measured.

The assay of the present invention may be a screen, whereby a number of agents are tested. In one aspect, the assay method of the present invention is a high through put screen.

Techniques for drug screening may be based on the method described in Geysen, European Patent Application 84/03564, published on Sep. 13, 1984. In summary, large numbers of different small peptide test compounds are synthesised on a solid substrate, such as plastic pins or some other surface. The peptide test compounds are reacted with a suitable target or fragment thereof and washed. Bound entities are then detected—such as by appropriately adapting methods well known in the art. A purified target can also be coated directly onto plates for use in a drug screening techniques. Alternatively, non-neutralising antibodies can be used to capture the peptide and immobilise it on a solid support.

This invention also contemplates the use of competitive drug screening assays in which neutralising antibodies capable of binding a target specifically compete with a test compound for binding to a target.

Another technique for screening provides for high throughput screening (HTS) of agents having suitable binding affinity to the substances and is based upon the method described in detail in WO 84/03564.

It is expected that the assay methods of the present invention will be suitable for both small and large-scale screening of test compounds as well as in quantitative assays.

In one preferred aspect, the present invention relates to a method of identifying agents that selectively modulate STS, which compounds have the formula (Ia).
Reporters A wide variety of reporters may be used in the assay methods (as well as screens) of the present invention with preferred reporters providing conveniently detectable signals (e.g. by spectroscopy). By way of example, a reporter gene may encode an enzyme which catalyses a reaction which alters light absorption properties.

Other protocols include enzyme-linked immunosorbent assay (ELISA), radioimmunoassay (RIA) and fluorescent activated cell sorting (FACS). A two-site, monoclonal-based immunoassay utilising monoclonal antibodies reactive to two non-interfering epitopes may even be used. These and other assays are described, among other places, in Hampton R et al (1990, Serological Methods, A Laboratory Manual, APS Press, St Paul Minn.) and Maddox D E et al (1983, J Exp Med 15 8:121 1).

Examples of reporter molecules include but are not limited to (β-galactosidase, invertase, green fluorescent protein, luciferase, chloramphenicol, acetyltransferase, (-glucuronidase, exo-glucanase and glucoamylase. Alternatively, radiolabelled or fluorescent tag-labelled nucleotides can be incorporated into nascent transcripts which are then identified when bound to oligonucleotide probes.

By way of further examples, a number of companies such as Pharmacia Biotech (Piscataway, N.J.), Promega (Madison, Wis.), and US Biochemical Corp (Cleveland, Ohio) supply commercial kits and protocols for assay procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. No. 3,817,837; U.S. Pat. No. 3,850,752; U.S. Pat. No. 3,939,350; U.S. Pat. No. 3,996,345; U.S. Pat. No. 4,277,437; U.S. Pat. No. 4,275,149 and U.S. Pat. No. 4,366,241.
Host Cells The term "host cell"—in relation to the present invention includes any cell that could comprise the target for the agent of the present invention.

Thus, a further embodiment of the present invention provides host cells transformed or transfected with a polynucleotide that is or expresses the target of the present invention. Preferably said polynucleotide is carried in a vector for the replication and expression of polynucleotides that are to be the target or are to express the target. The cells will be chosen to be compatible with the said vector and may for example be prokaryotic (for example bacterial), fungal, yeast or plant cells.

The gram negative bacterium *E. coli* is widely used as a host for heterologous gene expression. However, large amounts of heterologous protein tend to accumulate inside the cell. Subsequent purification of the desired protein from the bulk of *E. coli* intracellular proteins can sometimes be difficult.

In contrast to *E. coli*, bacteria from the genus *Bacillus* are very suitable as heterologous hosts because of their capability to secrete proteins into the culture medium. Other bacteria suitable as hosts are those from the genera *Streptomyces* and *Pseudomonas*.

Depending on the nature of the polynucleotide encoding the polypeptide of the present invention, and/or the desirability for further processing of the expressed protein, eukaryotic hosts such as yeasts or other fungi may be preferred. In general, yeast cells are preferred over fungal cells because they are easier to manipulate. However, some proteins are either poorly secreted from the yeast cell, or in some cases are not processed properly (e.g. hyperglycosylation in yeast). In these instances, a different fungal host organism should be selected.

Examples of suitable expression hosts within the scope of the present invention are fungi such as *Aspergillus* species (such as those described in EP-A-0184438 and EP-A-0284603) and *Trichoderma* species; bacteria such as *Bacillus* species (such as those described in EP-A-0134048 and EP-A-0253455), *Streptomyces* species and *Pseudomonas* species; and yeasts such as *Kluyveromyces* species (such as those described in EP-A-0096430 and EP-A-0301670) and *Saccharomyces* species. By way of example, typical expression hosts may be selected from *Aspergillus niger, Aspergillus niger* var. *tubigenis, Aspergillus niger* var. *awamori, Aspergillus aculeatis, Aspergillus nidulans, Aspergillus orvzae, Trichoderma reesei, Bacillus subtilis, Bacillus licheniformis, Bacillus amyloliquefaciens, Kluyveromyces lactis* and *Saccharomyces cerevisiae*.

The use of suitable host cells—such as yeast, fungal and plant host cells—may provide for post-translational modifications (e.g. myristoylation, glycosylation, truncation, lapidation and tyrosine, serine or threonine phosphorylation) as may be needed to confer optimal biological activity on recombinant expression products of the present invention.

Organism

The term "organism" in relation to the present invention includes any organism that could comprise the target according to the present invention and/or products obtained therefrom. Examples of organisms may include a fungus, yeast or a plant.

The term "transgenic organism" in relation to the present invention includes any organism that comprises the target according to the present invention and/or products obtained.

Transformation of Host Cells/Host Organisms

As indicated earlier, the host organism can be a prokaryotic or a eukaryotic organism. Examples of suitable prokaryotic hosts include *E. coli* and *Bacillus subtilis*. Teachings on the transformation of prokaryotic hosts is well documented in the art, for example see Sambrook et al (Molecular Cloning: A Laboratory Manual, 2nd edition, 1989, Cold Spring Harbor Laboratory Press) and Ausubel et al., Current Protocols in Molecular Biology (1995), John Wiley & Sons, Inc.

If a prokaryotic host is used then the nucleotide sequence may need to be suitably modified before transformation—such as by removal of introns.

In another embodiment the transgenic organism can be a yeast. In this regard, yeast have also been widely used as a vehicle for heterologous gene expression. The species *Saccharomyces cerevisiae* has a long history of industrial use, including its use for heterologous gene expression. Expression of heterologous genes in *Saccharomyces cerevisiae* has been reviewed by Goodey et al (1987, Yeast Biotechnology, D R Berry et al, eds, pp 401–429, Allen and Unwin, London) and by King et al (1989, Molecular and Cell Biology of Yeasts, E F Walton and G T Yarronton, eds, pp 107–133, Blackie, Glasgow).

For several reasons *Saccharomyces cerevisiae* is well suited for heterologous gene expression. First, it is non-pathogenic to humans and it is incapable of producing certain endotoxins. Second, it has a long history of safe use following centuries of commercial exploitation for various purposes. This has led to wide public acceptability. Third, the extensive commercial use and research devoted to the organism has resulted in a wealth of knowledge about the genetics and physiology as well as large-scale fermentation characteristics of *Saccharomyces cerevisiae*.

A review of the principles of heterologous gene expression in *Saccharomyces cerevisiae* and secretion of gene products is given by E Hinchcliffe E Kenny (1993, "Yeast as a vehicle for the expression of heterologous genes", Yeasts, Vol 5, Anthony H Rose and J Stuart Harrison, eds, 2nd edition, Academic Press Ltd.).

Several types of yeast vectors are available, including integrative vectors, which require recombination with the host genome for their maintenance, and autonomously replicating plasmid vectors.

In order to prepare the transgenic *Saccharomyces*, expression constructs are prepared by inserting the nucleotide sequence into a construct designed for expression in yeast. Several types of constructs used for heterologous expression have been developed. The constructs contain a promoter active in yeast fused to the nucleotide sequence, usually a promoter of yeast origin, such as the GAL1 promoter, is used. Usually a signal sequence of yeast origin, such as the sequence encoding the SUC2 signal peptide, is used. A terminator active in yeast ends the expression system.

For the transformation of yeast several transformation protocols have been developed. For example, a transgenic *Saccharomyces* according to the present invention can be prepared by following the teachings of Hinnen et al (1978, Proceedings of the National Academy of Sciences of the USA 75, 1929); Beggs, J D (1978, Nature, London, 275, 104); and Ito, H et al (1983, J Bacteriology 153, 163–168).

The transformed yeast cells are selected using various selective markers. Among the markers used for transformation are a number of auxotrophic markers such as LEU2, HIS4 and TRP1, and dominant antibiotic resistance markers such as aminoglycoside antibiotic markers, e.g. G418.

Another host organism is a plant. The basic principle in the construction of genetically modified plants is to insert genetic information in the plant genome so as to obtain a stable maintenance of the inserted genetic material. Several techniques exist for inserting the genetic information, the two main principles being direct introduction of the genetic information and introduction of the genetic information by use of a vector system. A review of the general techniques may be found in articles by Potrykus (Annu Rev Plant Physiol Plant Mol Biol [1991] 42:205–225) and Christou (Agro-Food-Industry Hi-Tech March/April 1994 17–27). Further teachings on plant transformation may be found in EP-A-0449375.

Thus, the present invention also provides a method of transforming a host cell with a nucleotide sequence that is to be the target or is to express the target. Host cells transformed with the nucleotide sequence may be cultured under conditions suitable for the expression of the encoded protein. The protein produced by a recombinant cell may be displayed on the surface of the cell. If desired, and as will be understood by those of skill in the art, expression vectors containing coding sequences can be designed with signal sequences which direct secretion of the coding sequences through a particular prokaryotic or eukaryotic cell membrane. Other recombinant constructions may join the coding sequence to nucleotide sequence encoding a polypeptide domain which will facilitate purification of soluble proteins (Kroll D J et al (1993) DNA Cell Biol 12:441–53).

Variants/Homologues/Derivatives

In addition to the specific amino acid sequences and nucleotide sequences mentioned herein, the present invention also encompasses the use of variants, homologue and derivatives thereof. Here, the term "homology" can be equated with "identity".

In the present context, an homologous sequence is taken to include an amino acid sequence which may be at least 75, 85 or 90% identical, preferably at least 95 or 98% identical. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is -12 for a gap and -4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403–410) and the GENEWORKS suite of comparison tools. Both BLAST and FASTA are available for offline and online searching (see Ausubel et al., 1999 ibid, pages 7–58 to 7–60). However it is preferred to use the GCG Bestfit program.

A further useful reference is that found in FEMS Microbiol Lett 1999 May 15;174(2):247–50 (and a published erratum appears in FEMS Microbiol Lett 1999 Aug. 1;177(1):187–8).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

Expression Vectors

The nucleotide sequence for use as the target or for expressing the target can be incorporated into a recombinant replicable vector. The vector may be used to replicate and express the nucleotide sequence in and/or from a compatible host cell. Expression may be controlled using control sequences which include promoters/enhancers and other expression regulation signals. Prokaryotic promoters and promoters functional in eukaryotic cells may be used. Tissue specific or stimuli specific promoters may be used. Chimeric promoters may also be used comprising sequence elements from two or more different promoters described above.

The protein produced by a host recombinant cell by expression of the nucleotide sequence may be secreted or may be contained intracellularly depending on the sequence and/or the vector used. The coding sequences can be designed with signal sequences which direct secretion of the substance coding sequences through a particular prokaryotic or eukaryotic cell membrane.

Fusion Proteins

The target amino acid sequence may be produced as a fusion protein, for example to aid in extraction and purification. Examples of fusion protein partners include glutathione-S-transferase (GST), 6xHis, GAL4 (DNA binding and/or transcriptional activation domains) and (-galactosidase. It may also be convenient to include a proteolytic cleavage site between the fusion protein partner and the protein sequence of interest to allow removal of fusion protein sequences. Preferably the fusion protein will not hinder the activity of the target.

The fusion protein may comprise an antigen or an antigenic determinant fused to the substance of the present invention. In this embodiment, the fusion protein may be a non-naturally occurring fusion protein comprising a substance which may act as an adjuvant in the sense of providing a generalised stimulation of the immune system. The antigen or antigenic determinant may be attached to either the amino or carboxy terminus of the substance.

In another embodiment of the invention, the amino acid sequence may be ligated to a heterologous sequence to encode a fusion protein. For example, for screening of peptide libraries for agents capable of affecting the substance activity, it may be useful to encode a chimeric substance expressing a heterologous epitope that is recognised by a commercially available antibody.

Therapy

The compounds of the present invention may be used as therapeutic agents—i.e. in therapy applications.

The term "therapy" includes curative effects, alleviation effects, and prophylactic effects.

The therapy may be on humans or animals, preferably female animals.

Pharmaceutical Compositions

In one aspect, the present invention provides a pharmaceutical composition, which comprises a compound according to the present invention and optionally a pharmaceutically acceptable carrier, diluent or excipient (including combinations thereof).

The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985.) The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilisers, dyes and even flavouring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition of the present invention may be formulated to be delivered using a mini-pump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be delivered by both routes.

Where the agent is to be delivered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

Combination Pharmaceutical

The compound of the present invention may be used in combination with one or more other active agents, such as one or more other pharmaceutically active agents.

By way of example, the compounds of the present invention may be used in combination with other STS inhibitors and/or other inhibitors such as an aromatase inhibitor (such as for example, 4hydroxyandrostenedione (4-OHA)) and/or steroids—such as the naturally occurring sterneurosteroids dehydroepiandrosterone sulfate (DHEAS) and pregnenolone sulfate (PS) and/or other structurally similar organic compounds.

In addition, or in the alternative, the compound of the present invention may be used in combination with a biological response modifier.

The term biological response modifier ("BRM") includes cytokines, immune modulators, growth factors, haematopoiesis regulating factors, colony stimulating factors, chemotactic, haemolytic and thrombolytic factors, cell surface receptors, ligands, leukocyte adhesion molecules, monoclonal antibodies, preventative and therapeutic vaccines, hormones, extracellular matrix components, fibronectin, etc. For some applications, preferably, the biological response modifier is a cytokine. Examples of cytokines include: interleukins (IL)—such as IL-1, IL-2, IL-3, IL-4, IL-5, IL-6, IL-7, IL-8, IL-9, IL-10, IL-11, IL-12, IL-19; Tumour Necrosis Factor (TNF)—such as TNF-$\alpha$; Interferon alpha, beta and gamma; TGF-$\beta$. For some applications, preferably the cytokine is tumour necrosis factor (TNF). For some applications, the TNF may be any type of TNF—such as TNF-$\alpha$, TNF-$\beta$, including derivatives or mixtures thereof. More preferably the cytokine is TNF-$\alpha$. Teachings on TNF may be found in the art—such as WO-A-98/08870 and WO-A-98/13348.

Administration

Typically, a physician will determine the actual dosage which will be most suitable for an individual subject and it will vary with the age, weight and response of the particular patient. The dosages below are exemplary of the average case. There can, of course, be individual instances where higher or lower dosage ranges are merited.

The compositions of the present invention may be administered by direct injection. The composition may be formulated for parenteral, mucosal, intramuscular, intravenous, subcutaneous, intraocular or transdermal administration. Depending upon the need, the agent may be administered at a dose of from 0.01 to 30 mg/kg body weight, such as from 0.1 to 10 mg/kg, more preferably from 0.1 to 1 mg/kg body weight.

By way of further example, the agents of the present invention may be administered in accordance with a regimen of 1 to 4 times per day, preferably once or twice per day. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Aside from the typical modes of delivery—indicated above—the term "administered" also includes delivery by techniques such as lipid mediated transfection, liposomes, immunoliposomes, lipofectin, cationic facial amphiphiles (CFAs) and combinations thereof. The routes for such delivery mechanisms include but are not limited to mucosal, nasal, oral, parenteral, gastrointestinal, topical, or sublingual routes.

The term "administered" includes but is not limited to delivery by a mucosal route, for example, as a nasal spray or aerosol for inhalation or as an ingestable solution; a parenteral route where delivery is by an injectable form, such as, for example, an intravenous, intramuscular or subcutaneous route.

Thus, for pharmaceutical administration, the STS inhibitors of the present invention can be formulated in any suitable manner utilising conventional pharmaceutical formulating techniques and pharmaceutical carriers, adjuvants, excipients, diluents etc. and usually for parenteral administration. Approximate effective dose rates may be in the range from 1 to 1000 mg/day, such as from 10 to 900 mg/day or even from 100 to 800 mg/day depending on the individual activities of the compounds in question and for a patient of average (70 Kg) bodyweight. More usual dosage rates for the preferred and more active compounds will be in the range 200 to 800 mg/day, more preferably, 200 to 500 mg/day, most preferably from 200 to 250 mg/day. They may be given in single dose regimes, split dose regimes and/or in multiple dose regimes lasting over several days. For oral administration they may be formulated in tablets, capsules, solution or suspension containing from 100 to 500 mg of compound per unit dose. Alternatively and preferably the compounds will be formulated for parenteral administration in a suitable parenterally administrable carrier and providing single daily dosage rates in the range 200 to 800 mg, preferably 200 to 500, more preferably 200 to 250 mg. Such effective daily doses will, however, vary depending on inherent activity of the active ingredient and on the bodyweight of the patient, such variations being within the skill and judgement of the physician.

Cell Cycling

The compounds of the present invention may be useful in the method of treatment of a cell cycling disorder.

As discussed in "Molecular Cell Biology" 3rd Ed. Lodish et al. pages 177–181 different eukaryotic cells can grow and divide at quite different rates. Yeast cells, for example, can divide every 120 min., and the first divisions of fertilised eggs in the embryonic cells of sea urchins and insects take only 1530 min. because one large pre-existing cell is subdivided. However, most growing plant and animal cells take 10–20 hours to double in number, and some duplicate at a much slower rate. Many cells in adults, such as nerve cells and striated muscle cells, do not divide at all; others, like the fibroblasts that assist in healing wounds, grow on demand but are otherwise quiescent.

Still, every eukaryotic cell that divides must be ready to donate equal genetic material to two daughter cells. DNA synthesis in eukaryotes does not occur throughout the cell division cycle but is restricted to a part of it before cell division.

The relationship between eukaryotic DNA synthesis and cell division has been thoroughly analysed in cultures of mammalian cells that were all capable of growth and division. In contrast to bacteria, it was found, eukaryotic cells spend only a part of their time in DNA synthesis, and it is completed hours before cell division (mitosis). Thus a gap of time occurs after DNA synthesis and before cell division; another gap was found to occur after division and before the next round of DNA synthesis. This analysis led to the conclusion that the eukaryotic cell cycle consists of an M (mitotic) phase, a $G_1$ phase (the first gap), the S (DNA synthesis) phase, a $G_2$ phase (the second gap), and back to M. The phases between mitoses ($G_1$, S, and $G_2$) are known collectively as the interphase.

Many nondividing cells in tissues (for example, all quiescent fibroblasts) suspend the cycle after mitosis and just prior to DNA synthesis; such "resting" cells are said to have exited from the cell cycle and to be in the $G_0$ state.

It is possible to identify cells when they are in one of the three interphase stages of the cell cycle, by using a fluorescence-activated cell sorter (FACS) to measure their relative DNA content: a cell that is in $G_1$ (before DNA synthesis) has a defined amount x of DNA; during S (DNA replication), it has between x and 2x; and when in $G_2$ (or M), it has 2x of DNA.

The stages of mitosis and cytokinesis in an animal cell are as follows (a) Interphase. The $G_2$ stage of interphase immediately precedes the beginning of mitosis. Chromosomal DNA has been replicated and bound to protein during the S phase, but chromosomes are not yet seen as distinct structures. The nucleolus is the only nuclear substructure that is visible under light microscope. In a diploid cell before DNA replication there are two morphologic chromosomes of each type, and the cell is said to be 2n. In $G_2$, after DNA replication, the cell is 4n. There are four copies of each chromosomal DNA. Since the sister chromosomes have not yet separated from each other, they are called sister chromatids.

b) Early prophase. Centrioles, each with a newly formed daughter centriole, begin moving toward opposite poles of the cell; the chromosomes can be seen as long threads. The nuclear membrane begins to disaggregate into small vesicles.

(c) Middle and late prophase. Chromosome condensation is completed; each visible chromosome structure is composed of two chromatids held together at their centromeres. Each chromatid contains one of the two newly replicated daughter DNA molecules. The microtubular spindle begins to radiate from the regions just adjacent to the centrioles, which are moving closer to their poles. Some spindle fibres reach from pole to pole; most go to chromatids and attach at kinetochores.

(d) Metaphase. The chromosomes move toward the equator of the cell, where they become aligned in the equatorial plane. The sister chromatids have not yet separated.

(e) Anaphase The two sister chromatids separate into independent chromosomes Each contains a centromere that is linked by a spindle fibre to one pole, to which it moves. Thus one copy of each chromosome is donated to each daughter cell. Simultaneously, the cell elongates, as do the pole-to-pole spindles. Cytokinesis begins as the cleavage furrow starts to form.

(f) Telophase. New membranes form around the daughter nuclei; the chromosomes uncoil and become less distinct, the nucleolus becomes visible again, and the nuclear membrane forms around each daughter nucleus. Cytokinesis is nearly complete, and the spindle disappears as the microtubules and other fibres depolymerise. Throughout mitosis the "daughter" centriole at each pole grows until it is full-length. At telophase the duplication of each of the original centrioles is completed, and new daughter centrioles will be generated during the next interphase.

(g) Interphase. Upon the completion of cytokinesis, the cell enters the $G_1$ phase of the cell cycle and proceeds again around the cycle.

It will be appreciated that cell cycling is an extremely important cell process. Deviations from normal cell cycling can result in a number of medical disorders. Increased and/or unrestricted cell cycling may result in cancer. Reduced cell cycling may result in degenerative conditions. Use of the compound of the present invention may provide a means to treat such disorders and conditions.

Thus, the compound of the present invention may be suitable for use in the treatment of cell cycling disorders such as cancers, including hormone dependent and hormone independent cancers.

In addition, the compound of the present invention may be suitable for the treatment of cancers such as breast cancer, ovarian cancer, endometrial cancer, sarcomas, melanomas, prostate cancer, pancreatic cancer etc. and other solid tumours.

For some applications, cell cycling is inhibited and/or prevented and/or arrested, preferably wherein cell cycling is prevented and/or arrested. In one aspect cell cycling may be inhibited and/or prevented and/or arrested in the $G_2/M$ phase. In one aspect cell cycling may be irreversibly prevented and/or inhibited and/or arrested, preferably wherein cell cycling is irreversibly prevented and/or arrested.

By the term "irreversibly prevented and/or inhibited and/ or arrested" it is meant after application of a compound of the present invention, on removal of the compound the effects of the compound, namely prevention and/or inhibition and/or arrest of cell cycling, are still observable. More particularly by the term "irreversibly prevented and/or inhibited and/or arrested" it is meant that when assayed in accordance with the cell cycling assay protocol presented herein, cells treated with a compound of interest show less growth after Stage 2 of the protocol 1 than control cells. Details on this protocol are presented below.

Thus, the present invention provides compounds which: cause inhibition of growth of oestrogen receptor positive (ER+) and ER negative (ER−) breast cancer cells in vitro by preventing and/or inhibiting and/or arresting cell cycling; and/or cause regression of nitrosomethyl urea (NMU)-induced mammary tumours in intact animals (i.e. not ovariectomised), and/or prevent and/or inhibit and/or arrest cell cycling in cancer cells; and/or act in vivo by preventing and/or inhibiting and/or arresting cell cycling and/or act as a cell cycling agonist.

Cell Cycling Assay (Protocol 6)
Procedure
Stage 1

MCF-7 breast cancer cells are seeded into multi-well culture plates at a density of 105 cells/well. Cells were allowed to attach and grown until about 30% confluent when they are treated as follows:

Control—no treatment

Compound of Interest (COI) 20 $\mu$M

Cells are grown for 6 days in growth medium containing the COI with changes of medium/COI every 3 days. At the end of this period cell numbers were counted using a Coulter cell counter.

Stage 2

After treatment of cells for a 6-day period with the COI cells are re-seeded at a density of $10^4$ cells/well. No further treatments are added. Cells are allowed to continue to grow for a further 6 days in the presence of growth medium. At the end of this period cell numbers are again counted.

Cancer

As indicated, the compounds of the present invention may be useful in the treatment of a cell cycling disorder. A particular cell cycling disorder is cancer.

Cancer remains a major cause of mortality in most Western countries. Cancer therapies developed so far have included blocking the action or synthesis of hormones to inhibit the growth of hormone-dependent tumours. However, more aggressive chemotherapy is currently employed for the treatment of hormone-independent tumours.

Hence, the development of a pharmaceutical for anti-cancer treatment of hormone dependent and/or hormone independent tumours, yet lacking some or all of the side-effects associated with chemotherapy, would represent a major therapeutic advance.

It is known that oestrogens undergo a number of hydroxylation and conjugation reactions after their synthesis. Until recently it was thought that such reactions were part of a metabolic process that ultimately rendered oestrogens water soluble and enhanced their elimination from the body. It is now evident that some hydroxy metabolites (e.g. 2-hydroxy and 16alpha-hydroxy) and conjugates (e.g. oestrone sulphate, E1S) are important in determining some of the complex actions that oestrogens have in the body.

Workers have investigated the formation of 2- and 16-hydroxylated oestrogens in relation to conditions that alter the risk of breast cancer. There is now evidence that factors which increase 2-hydroxylase activity are associated with a reduced cancer risk, while those increasing 16alpha-hydroxylation may enhance the risk of breast cancer. Further interest in the biological role of estrogen metabolites has been stimulated by the growing body of evidence that 2-methoxyoestradiol is an endogenous metabolite with anti-mitotic properties. 2-MeOE2 is formed from 2-hydroxy estradiol (2-OHE2) by catechol estrogen methyl transferase, an enzyme that is widely distributed throughout the body.

Workers have shown that in vivo 2-MeOE2 inhibits the growth of tumours arising from the subcutaneous injection of Meth A sarcoma, B16 melanoma or MDA-MB-435 estrogen receptor negative (ER−) breast cancer cells. It also inhibits endothelial cell proliferation and migration, and in vitro angiogenesis. It was suggested that the ability of 2-MeOE2 to inhibit tumour growth in vivo may be due to its ability to inhibit tumour-induced angiogenesis rather than direct inhibition of the proliferation of tumour cells.

The mechanism by which 2-MeOE2 exerts its potent anti-mitogenic and anti-angiogenic effects is still being elucidated. There is evidence that at high concentrations it can inhibit microtubule polymerisation and act as a weak inhibitor of colchicine binding to tubulin. Recently, however, at concentrations that block mitosis, tubulin filaments in cells were not found to be depolymerised but to have an identical morphology to that seen after taxol treatment. It is possible, therefore, that like taxol, a drug that is used for breast and ovarian breast cancer therapy, 2-MeOE2 acts by stabilising microtubule dynamics.

While the identification of 2-MeOE2 as a new therapy for cancer represents an important advance, the bioavailability of orally administered oestrogens is poor. Furthermore, they can undergo extensive metabolism during their first pass through the liver. As part of a research programme to develop a steroid sulphatase inhibitor for breast cancer therapy, oestrone-3-O-sulphamate (EMATE) was identified as a potent active site-directed inhibitor. Unexpectedly, EMATE proved to possess potent oestrogenic properties with its oral uterotrophic activity in rats being a 100-times higher than that of estradiol. Its enhanced oestrogenicity is thought to result from its absorption by red blood cells (rbcs) which protects it from inactivation during its passage through the liver and which act as a reservoir for its slow release for a prolonged period of time. A number of A-ring modified analogues were synthesised and tested, including 2-methoxyoestrone-3-O-sulphamate. While this compound was equipotent with EMATE as a steroid sulphatase inhibitor, it was devoid of oestrogenicity.

We believe that the compound of the present invention provides a means for the treatment of cancers and, especially, breast cancer.

In addition or in the alternative the compound of the present invention may be useful in the blocking the growth of cancers including leukaemias and solid tumours such as breast, endometrium, prostate, ovary and pancreatic tumours.

Therapy Concerning Oestrogen

We believe that some of the compounds of the present invention may be useful in the control of oestrogen levels in the body—in particular in females. Thus, some of the compounds may be useful as providing a means of fertility control—such as an oral contraceptive tablet, pill, solution or lozenge. Alternatively, the compound could be in the form of an implant or as a patch.

Thus, the compounds of the present invention may be useful in treating hormonal conditions associated with oestrogen.

In addition or in the alternative the compound of the present invention may be useful in treating hormonal conditions in addition to those associated with oestrogen. Hence, the compound of the present invention may also be capable of affecting hormonal activity and may also be capable of affecting an immune response.

Neurodegenerative Diseases

We believe that some of the compounds of the present invention may be useful in the treatment of neurodenerative diseases, and similar conditions.

By way of example, it is believed that STS inhibitors may be useful in the enhancing the memory function of patients suffering from illnesses such as amnesia, head injuries, Alzheimer's disease, epileptic dementia, presenile dementia, post traumatic dementia, senile dementia, vascular dementia and post-stroke dementia or individuals otherwise seeking memory enhancement.

TH1

We believe that some of the compounds of the present invention may be useful in TH1 implications.

By way of example, it is believed that the presence of STS inhibitors within the macrophage or other antigen presenting cells may lead to a decreased ability of sensitised T cells to mount a TH1 (high IL-2, IFN? low IL-4) response. The normal regulatory influence of other steroids such as glucocorticoids would therefore predominate.

Inflamatory Conditions

We believe that some of the compounds of the present invention may be useful in treating inflammatory conditions—such as conditions associated with any one or more of: autoimmunity, including for example, rheumatoid arthritis, type I and II diabetes, systemic lupus erythematosus, multiple sclerosis, myasthenia gravis, thyroiditis, vasculitis, ulcerative colitis and Crohn's disease, skin disorders e.g. psoriasis and contact dermatitis; graft versus host disease; eczema; asthma and organ rejection following transplantation.

By way of example, it is believed that STS inhibitors may prevent the normal physiological effect of DHEA or related steroids on immune and/or inflammatory responses.

The compounds of the present invention may be useful in the manufacture of a medicament for revealing an endogenous glucocorticoid-like effect.

Other Therapies

It is also to be understood that the compound/composition of the present invention may have other important medical implications.

For example, the compound or composition of the present invention may be useful in the treatment of the disorders listed in WO-A-99/52890—viz:

In addition, or in the alternative, the compound or composition of the present invention may be useful in the treatment of the disorders listed in WO-A-98/05635. For ease of reference, part of that list is now provided: cancer, inflammation or inflammatory disease, dermatological disorders, fever, cardiovascular effects, haemorrhage, coagulation and acute phase response, cachexia, anorexia, acute infection, HIV infection, shock states, graft-versus-host reactions, autoimmune disease, reperfusion injury, meningitis, migraine and aspirin-dependent anti-thrombosis; tumour growth, invasion and spread, angiogenesis, metastases, malignant, ascites and malignant pleural effusion; cerebral ischaemia, ischaemic heart disease, osteoarthritis, rheumatoid arthritis, osteoporosis, asthma, multiple sclerosis, neurodegeneration, Alzheimer's disease, atherosclerosis, stroke, vasculitis, Crohn's disease and ulcerative colitis; periodontitis, gingivitis; psoriasis, atopic dermatitis, chronic ulcers, epidermolysis bullosa; corneal ulceration, retinopathy and surgical wound healing; rhinitis, allergic conjunctivitis, eczema, anaphytaxis; restenosis, congestive heart failure, endometriosis, atherosclerosis or endosclerosis.

In addition, or in the alternative, the compound or composition of the present invention may be useful in the treatment of disorders listed in WO-A-98/07859. For ease of reference, part of that list is now provided: cytokine and cell proliferation/differentiation activity; immunosuppressant or immunostimulant activity (e.g. for treating immune deficiency, including infection with human immune deficiency virus; regulation of lymphocyte growth; treating cancer and many autoimmune diseases, and to prevent transplant rejection or induce tumour immunity); regulation of haematopoiesis, e.g. treatment of myeloid or lymphoid diseases; promoting growth of bone, cartilage, tendon, ligament and nerve tissue, e.g. for healing wounds, treatment of burns, ulcers and periodontal disease and neurodegeneration; inhibition or activation of follicle-stimulating hormone (modulation of fertility); chemotactic/chemokinetic activity (e.g. for mobilising specific cell types to sites of injury or infection); haemostatic and thrombolytic activity (e.g. for treating haemophilia and stroke); antiinflammatory activity (for treating e.g. septic shock or Crohn's disease); as antimicrobials; modulators of e.g. metabolism or behaviour; as analgesics; treating specific deficiency disorders; in treatment of e.g. psoriasis, in human or veterinary medicine.

In addition, or in the alternative, the composition of the present invention may be useful in the treatment of disorders listed in WO-A-98/09985. For ease of reference, part of that list is now provided: macrophage inhibitory and/or T cell inhibitory activity and thus, anti-inflammatory activity; anti-immune activity, i.e. inhibitory effects against a cellular and/or humoral immune response, including a response not associated with inflammation; inhibit the ability of macrophages and T cells to adhere to extracellular matrix components and fibronectin, as well as up-regulated fas receptor expression in T cells; inhibit unwanted immune reaction and inflammation including arthritis, including rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhinolaryngological diseases, dermatitis or other dermal diseases, periodontal diseases or other dental diseases, orchitis or epididimo-orchitis, infertility, orchidal trauma or other immune-related testicular diseases, placental dysfunction, placental insufficiency, habitual abortion, eclampsia, pre-eclampsia and other immune and/or inflammatory-related gynaecological diseases, posterior uveitis, intermediate uveitis, anterior uveitis, conjunctivitis, chorioretinitis, uveoretinitis, optic neuritis, intraocular inflammation, e.g. retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreo-retinopathies, acute ischaemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, subacute sclerosing pan-encephalitis, encephalomyelitis, acute neuropathy, subacute neuropathy, chronic neuropathy, Guillaim-Barre syndrome, Sydenham chora, myasthenia gravis, pseudo-tumour cerebri, Down's Syndrome, Huntington's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue.

Compound Preparation

The compounds of the present invention may be prepared by reacting an appropriate alcohol with a suitable chloride. By way of example, the sulphamate compounds of the present invention may be prepared by reacting an appropriate alcohol with a suitable sulfamoyl chloride, of the formula $R1R2NSO_2Cl$.

Typical conditions for carrying out the reaction are as follows.

Sodium hydride and a sulfamoyl chloride are added to a stirred solution of the alcohol in anhydrous dimethyl formamide at 0° C. Subsequently, the reaction is allowed to warm to room temperature whereupon stirring is continued for a further 24 hours. The reaction mixture is poured onto a cold saturated solution of sodium bicarbonate and the resulting aqueous phase is extracted with dichloromethane. The combined organic extracts are dried over anhydrous $MgSO_4$. Filtration followed by solvent evaporation in vacuo and co-evaporated with toluene affords a crude residue which is further purified by flash chromatography.

Preferably, the alcohol is derivatised, as appropriate, prior to reaction with the sulfamoyl chloride. Where necessary, functional groups in the alcohol may be protected in known manner and the protecting group or groups removed at the end of the reaction.

Preferably, the sulphamate compounds are prepared according to the teachings of Page et al (1990 Tetrahedron 46; 2059–2068).

The phosphonate compounds may be prepared by suitably combining the teachings of Page et al (1990 Tetrahedron 46; 2059–2068) and PCT/GB92/01586.

The sulphonate compounds may be prepared by suitably adapting the teachings of Page et al (1990 Tetrahedron 46; 2059–2068) and PCT/GB92/01586.

The thiophosphonate compounds may be prepared by suitably adapting the teachings of Page et al (1990 Tetrahedron 46; 2059–2068) and PCT/GB91/00270.

SUMMARY

In summation, the present invention provides novel compounds for use as steroid sulphatase inhibitors, and pharmaceutical compositions containing them.

Figure 2:
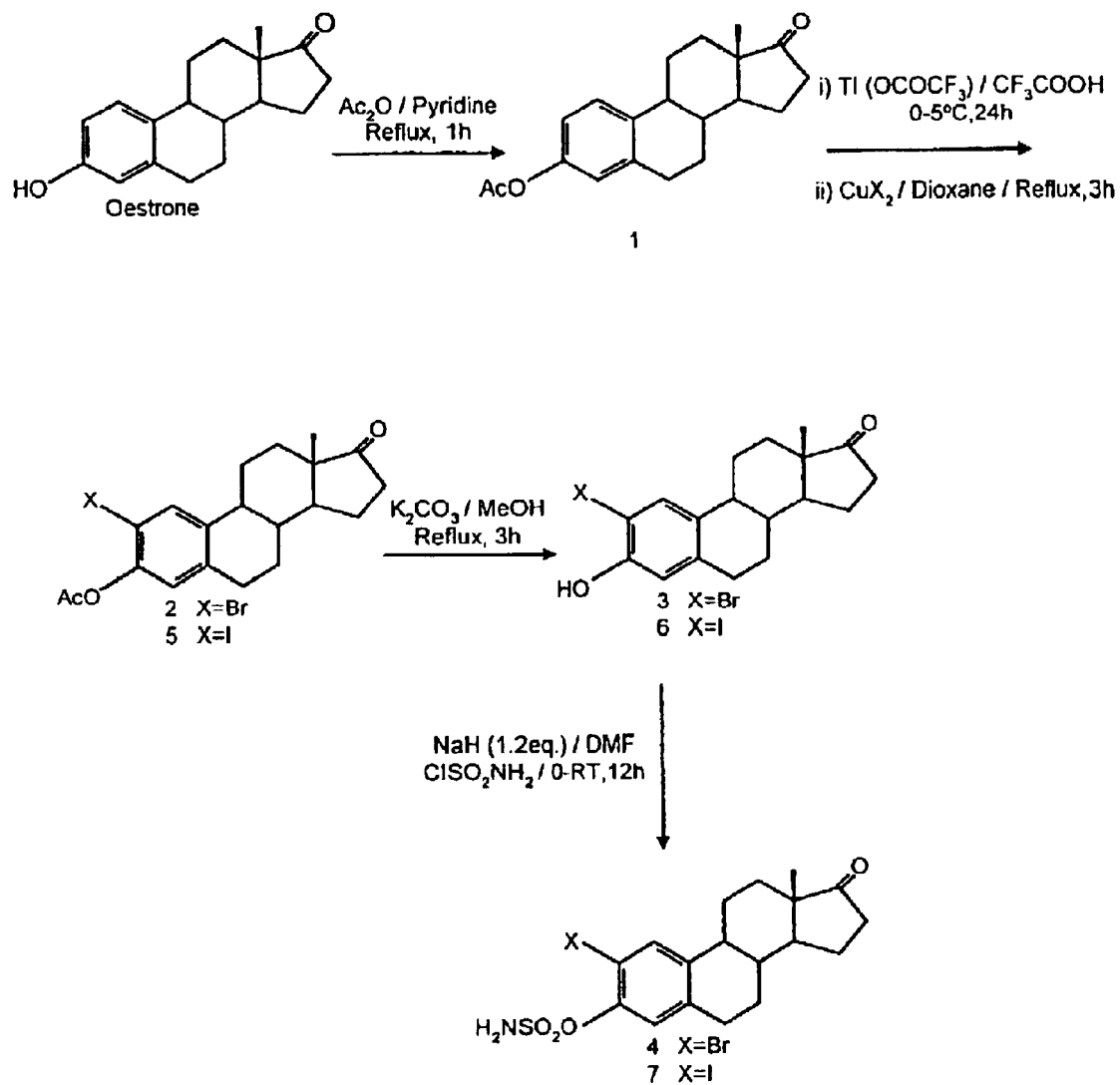
Figure 3:
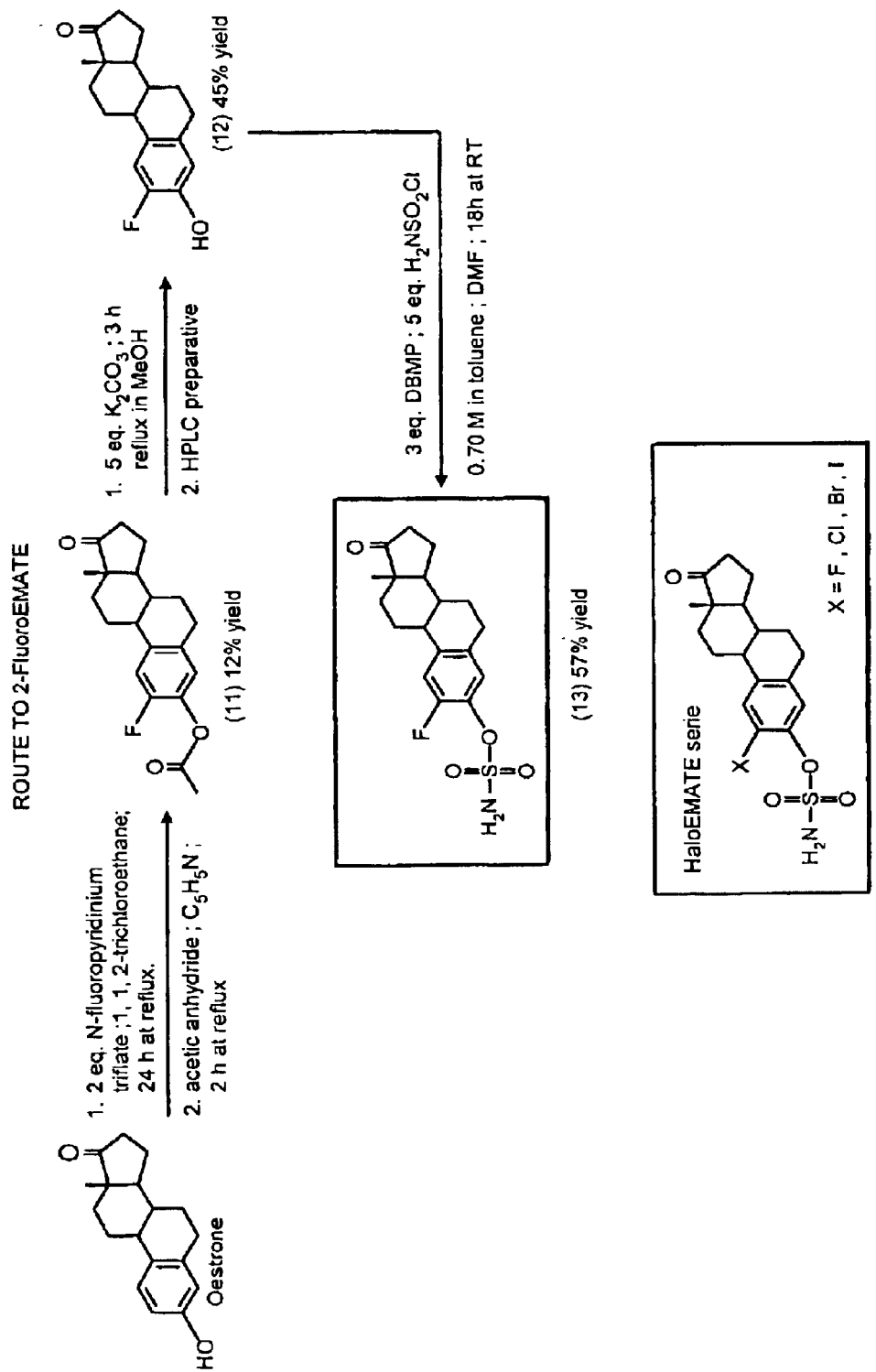
Figures 4, 5:
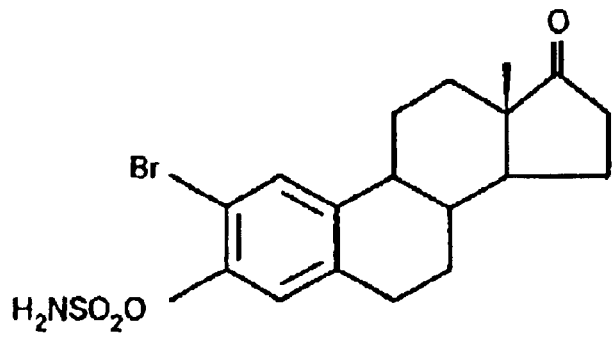
Figure 6:
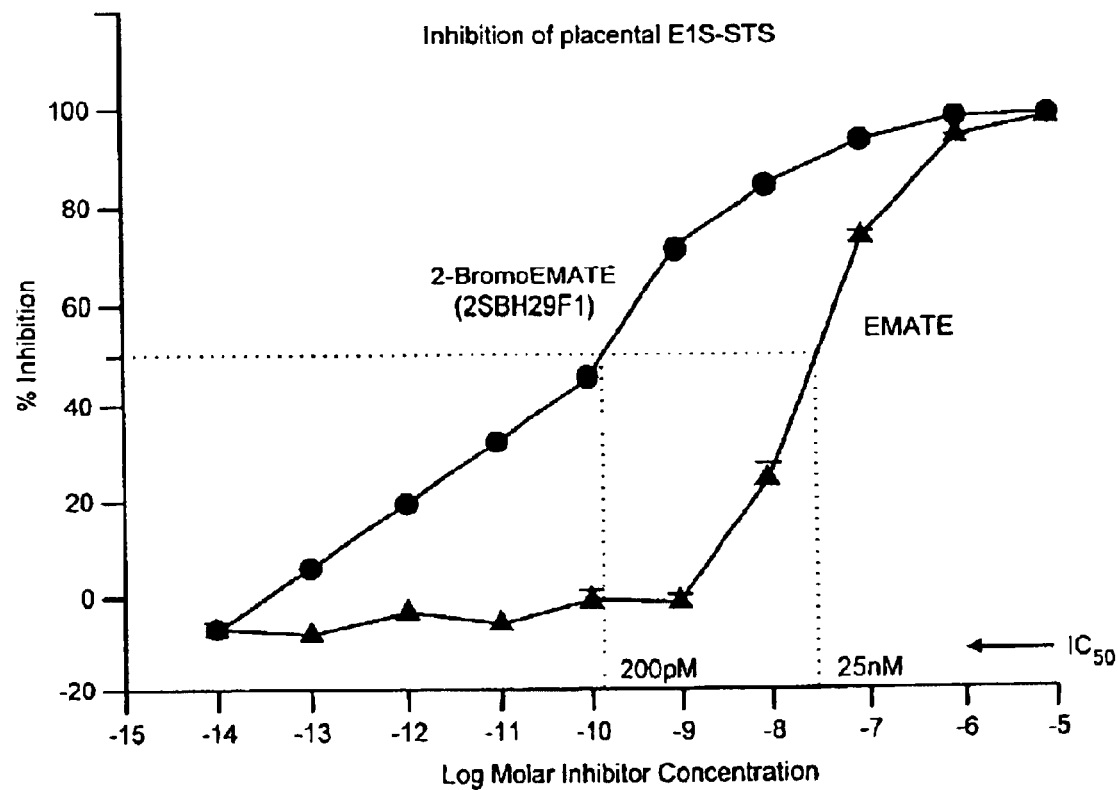
Figure 7:
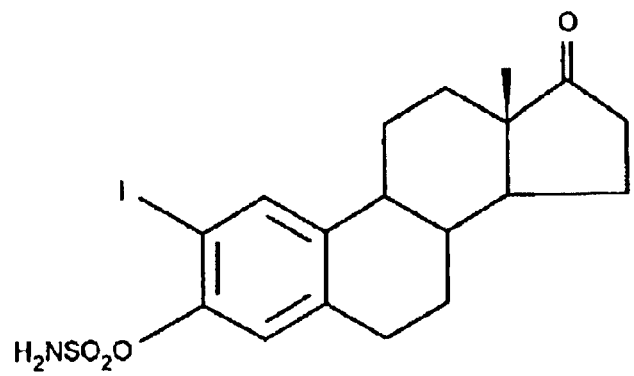
Figures 8, 9:
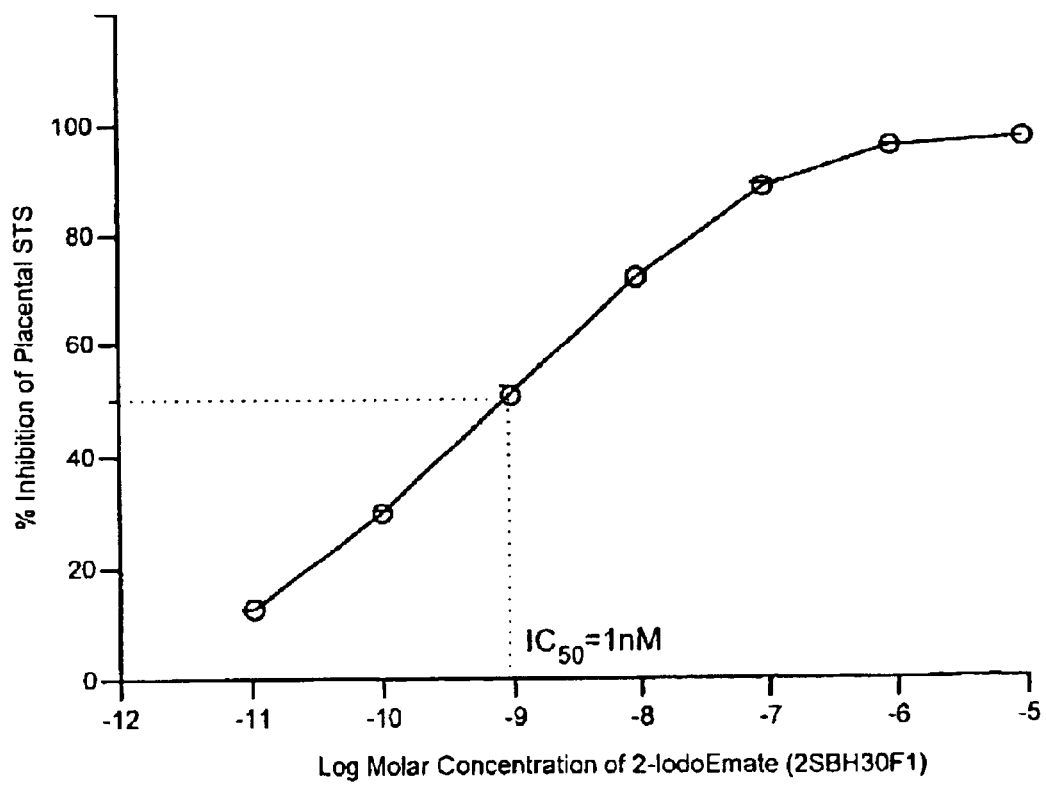
Figure 10:
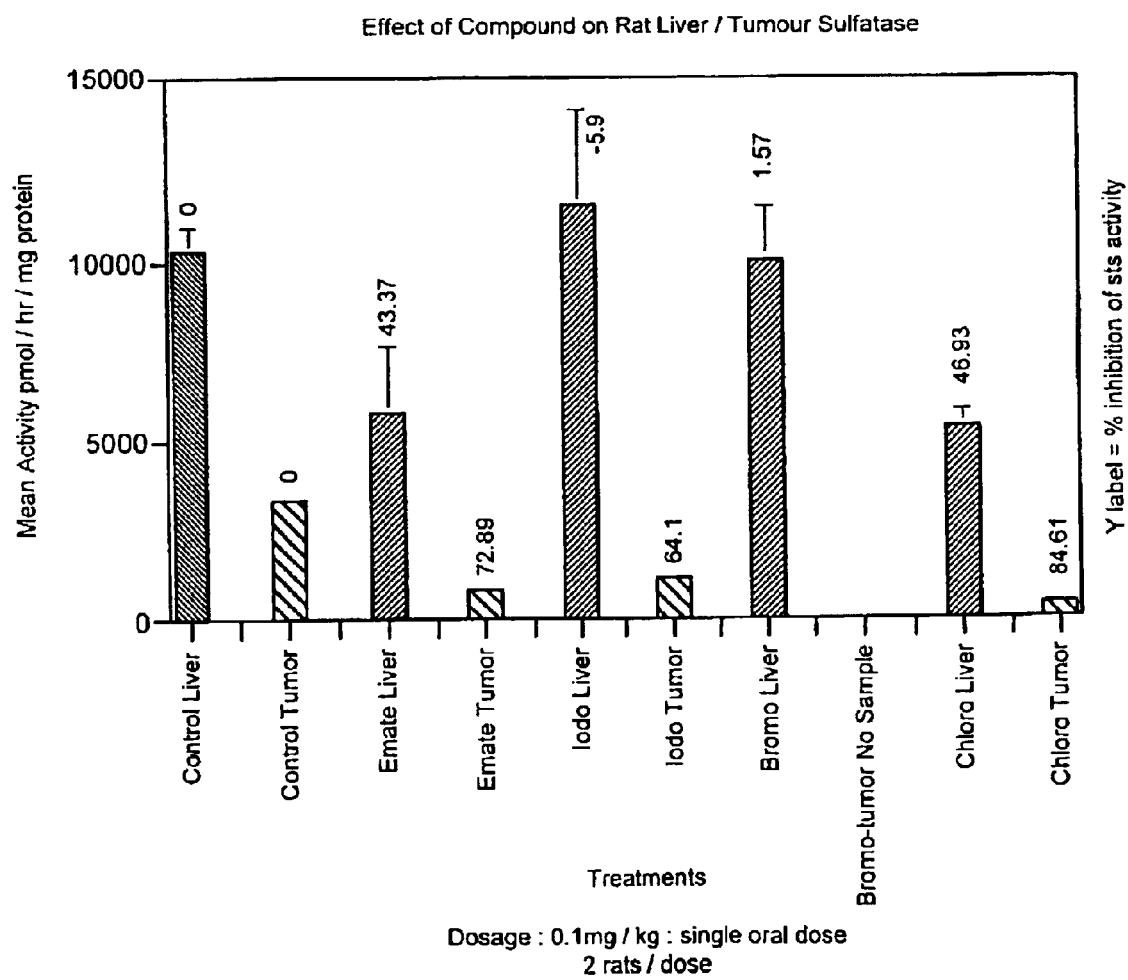
Figure 11:
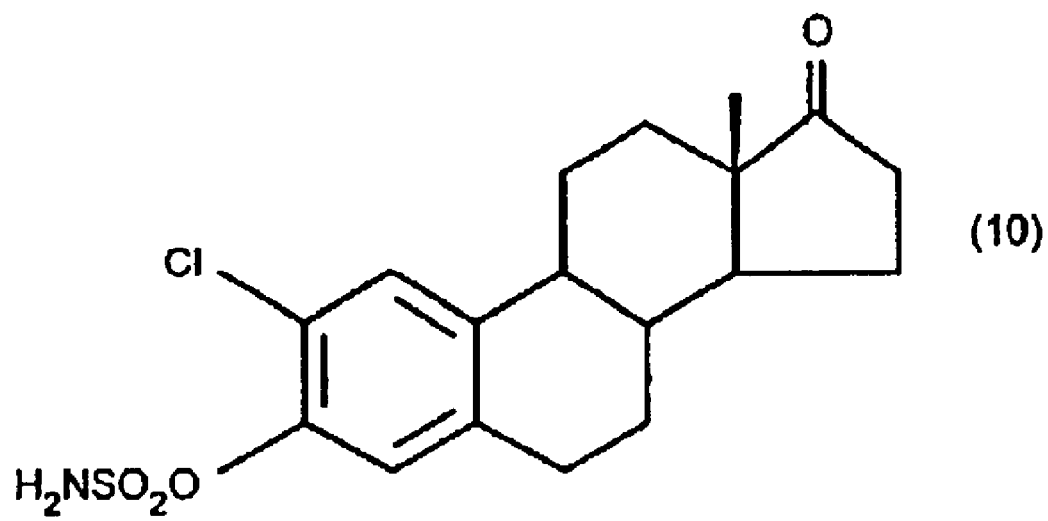
Figure 12:
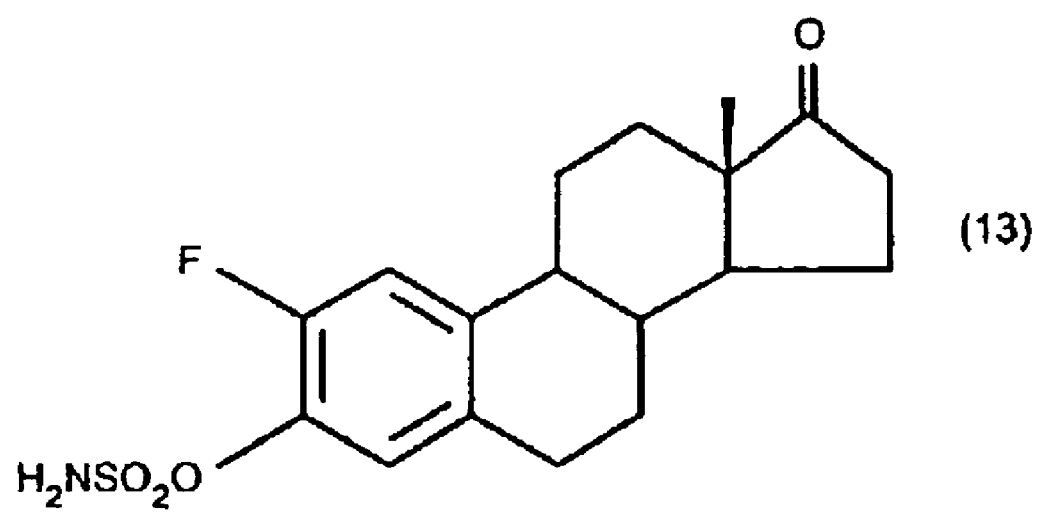
Figure 13:
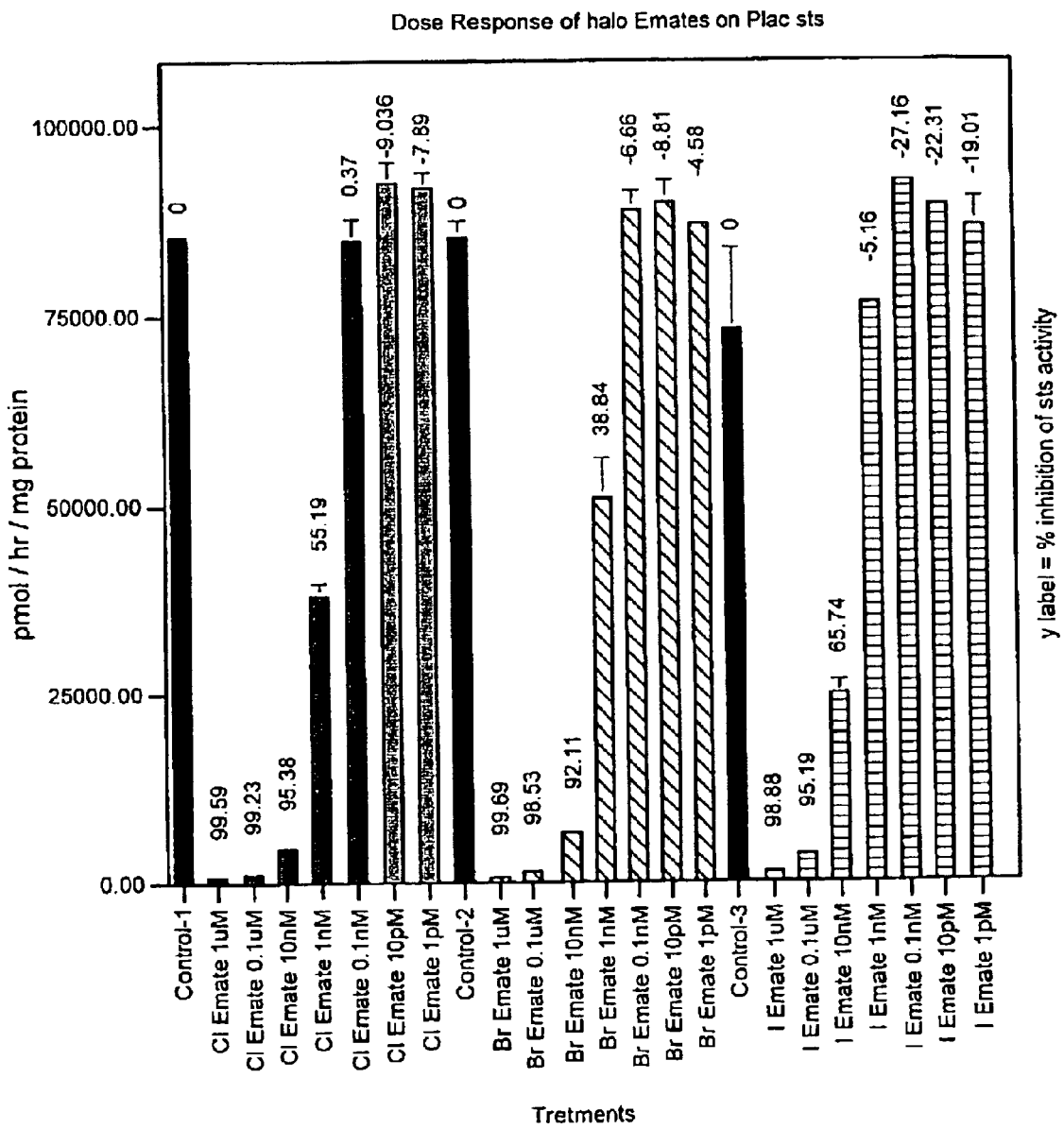

The present invention will now be described only by way of example with reference to the accompanying drawings in which:

FIG. 1 presents general formulae;

FIG. 2 presents a general reaction scheme;

FIG. 3 presents a general reaction scheme;

FIG. 4 presents a compound formula;

FIG. 5 presents a Table of data;

FIG. 6 presents a graph;

FIG. 7 presents a compound formula;

FIG. 8 presents a Table of data;

FIG. 9 presents a graph;

FIG. 10 presents a graph;

FIG. 11 presents a compound formula;

FIG. 12 presents a compound formula;

FIG. 13 presents a graph; and

Figure 14:
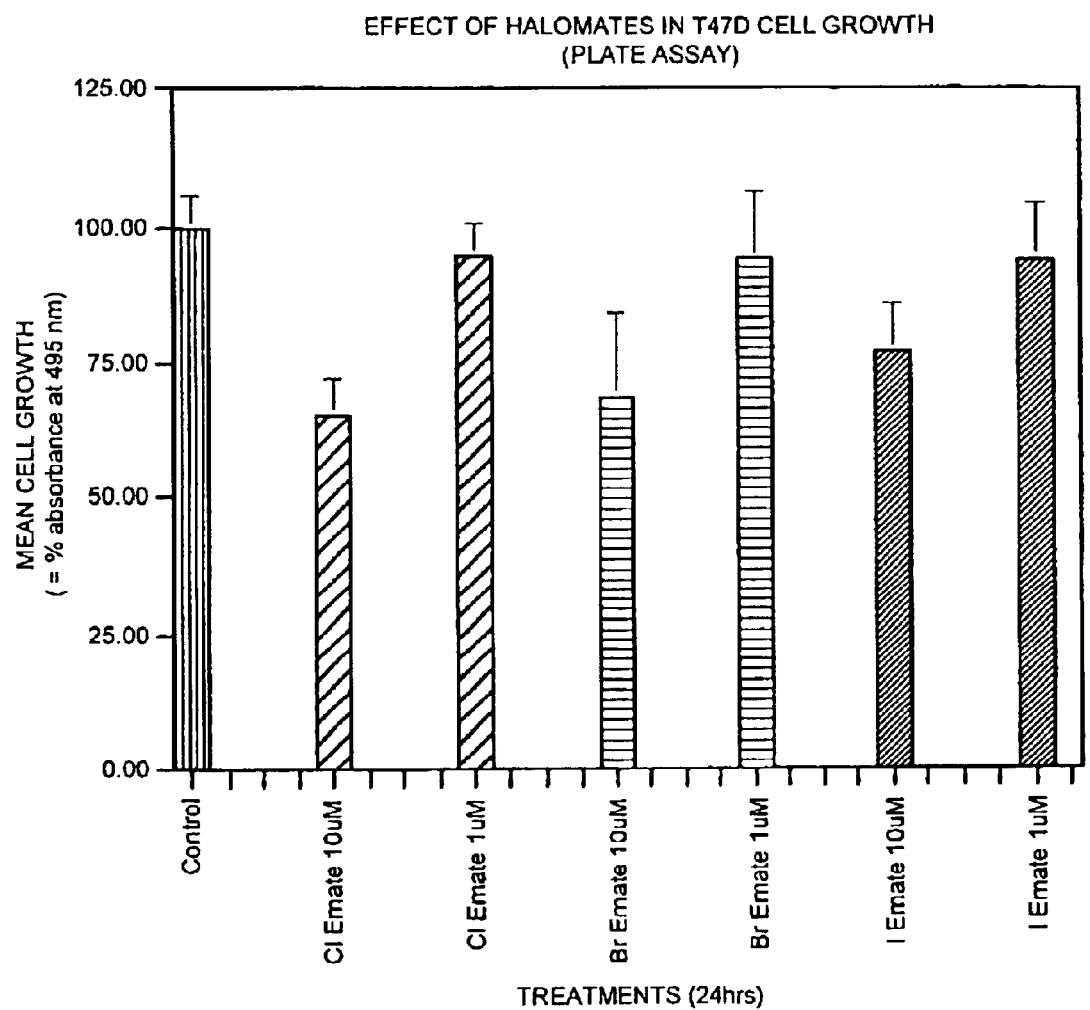

FIG. 14 presents a graph.

EXAMPLES

The following compounds according to the present invention (see FIGS. 4, 7, 11 and 12) were prepared according to general synthetic scheme presented in FIG. 2. In particular, Compounds 1, 2, 3, 5, 6, 8 and 9 (see Scheme 1 in FIG. 2) were prepared as described by Page et al. (Tetrahedron 1990; 46; 2059–2068).

Compounds were then tested according to the Protocols mentioned above. The results (see FIGS. 5, 6, 8, 9, 10, 13 and 14) showed that they were able to act as STS inhibitors.

The $IC_{50}$ of each of Compound 4, 7, 10 and 13 was also derived. These values are given below.

| Compound | | IC$_{50}$ |
|---|---|---|
| 4 | 2-BromoEMATE | 1.65 nM |
| 7 | 2-IodoEMATE | 6.1 nM |
| 10 | 2-ChloroEMATE | 0.8 nM |
| 13 | 2-FluoroMATE | 5.6 nM |

Oestrone Acetate (1)

A mixture of oestrone (10 g, 36.82 mmol), acetic anhydride (17.5 ml) and pyridine (75 ml) was heated under reflux for 2 h. The cooled reaction mixture was concentrated in vacuo and then quenched with ice-water. The precipitate that formed was filtered off, washed with water, dried, and recrystallised from aqueous ethanol (95%) to give 1 as white crystals (11.2 g, 97%); mp 115–118° C.; TLC (chloroform/acetone, 8:1): Rf 83; νmax (KBr) 1770, 1720 (C=O) cm$^{-1}$; $\delta_H$ (400 MHz, CDCl$_3$) 0.91 (3H, S, C-18-C$\underline{H}_3$), 1.42–2.19 (11H, m), 2.29 (3H, s, C$\underline{H}_3$CO), 2.38–2.54 (2H, m), 2.9 (2H, t, J=4.43 Hz, C-6-C$\underline{H}_2$), 6.81 (1H, d, $J_{C-2-H, C-4-H}$=2.14 Hz, C-4-$\underline{H}$), 6.86 (1H, dd, $J_{C-4-H, C-2-H}$=2.44 Hz and $J_{C-1-H, C-2-H}$=8.54 Hz, C-2-$\underline{H}$) and 7.28 (1H, d, $J_{C-2-H, C-1-H}$=8.24 Hz, C-1-$\underline{H}$); MS m/z (FAB+) 466.2 [10, (M+H+NBA)$^+$], 313.2 [65, (M+H)$^+$], 270.2 [100, (M+H−CH$_3$CO)$^+$]; MS m/z (FAB−) 269.2 [100, (M−CH$_3$CO)$^-$]. Found C, 76.9; H, 7.83 C$_{20}$H$_{24}$O$_3$ requires C, 76.89; H, 7.74%.

2-Bromooestrone Acetate (2)

To a solution of 1 (2.0 g, 6.402 mmol) in trifluoroacetic acid (TFA, 50 ml), thallic trifluoroacetate (6.958 g, 12.80 mmol) was added and the resulting mixture was stirred at 0° C. under nitrogen for 24 h. Upon removal of TFA under reduced pressure at <40° C., the crystalline oestrone-thallium (III) complex that obtained was washed twice with 1,2-dichloroethane. 1,4-Dioxane (30 ml) and copper bromide (8.58 g, 38.41 mmol) were then added to this washed complex and the resulting mixture was heated under reflux for 3 h. After evaporation of the solvent, water (100 ml) were then added to this washed complex After evaporation of the solvent, water (100 ml) was added to the residue resulted and the crude product was extracted into dichloromethane (3×150 ml). The combined organic extracts were washed with water, dried (MgSO$_4$), filtered and evaporated. The crude product obtained was fractionated by flash chromatography (ethyl acetate/hexane, 1:4) and the pale white solid obtained (2.05 g) was further purified by recrystallization from methanol to give 2 as colourless crystals (1.79 g, 72%); mp 229–231° C.; TLC (chloroform/acetone, 8:1 and ethyl cetate/hexane, 4:1); Rfs 0.89 and 0.62 respectively; νmax (KBr) 1770, 1730 (C=O) cm$^{-1}$; $\delta_H$ (400 MHz, CDCl$_3$) 0.91 (3H, s, C-18-C$\underline{H}_3$), 1.25–2.3 (12H, m), 2.34 (3H, s, C$\underline{H}_3$CO), 2.5 (1H, m), 2.86 (2H, t, J=4.58 Hz, C-6-C$\underline{H}_2$), 6.85 (1H, s, C-4-$\underline{H}$) and 7.49 (1H, s, C-1-$\underline{H}$); MS m/z (FAB+) 545.2 [90, (M+H+NBA)$^+$], 391.2 [100, (M)$^+$], 348.1 [90, (M−CH$_3$CO)$^+$], 330.1 (10); Acc. MS (FAB+) 391.08559 C$_{20}$H$_{24}$BrO$_3$ requires 391.09088. Found C, 61.2; H, 5.89; C$_{20}$H$_{23}$BrO$_3$ requires C, 61.39; H, 5.92%.

2-Brontooestrone (3)

A mixture of 3 (1.5 g, 3.832 mmol), potassium carbonate (2.65 g, 19.17 mmol) in methanol (70 ml) was heated under reflux for 3 h. Upon evaporation of the solvent, water (50 ml) was added to the residue obtained and the crude product was extracted with dichloromethane (3×100 ml). The combined organic extracts were washed with water, dried (MgSO$_4$), filtered and evaporated to give a yellow solid (1.3 g) which was purified by recrystallization from ethyl acetate/petroleum ether (60–80° C.) (3:2) to give 3 as pale yellow crystals (1.23 g, 93%) mp 190–193° C.; TLC (chloroform/acetone, 8:1 and 4:1): Rfs 0.51 and 0.64 respectively; νmax (KBr) 1710 (C=O) cm$^{-1}$; $\delta_H$ (400 MHz, CDCl$_3$) 0.87 (3H, s, C$\underline{H}_3$), 1.4–2.52 (13H, m), 2.84 (2H, m, C-6-C$\underline{H}_2$), 5.32 (1H, br s, exchanged with D$_2$O, O$\underline{H}$), 6.73 (1H, s, C-4-$\underline{H}$) and 7.52 (1H, s, C-1-$\underline{H}$); $\delta_C$ (400 MHz, CDCl$_3$) 13.81 (q, C-18), 21.56 (t), 25.89 (t), 26.26 (t), 29.9 (t), 31.54 (t), 31.91 (t), 38.04 (d), 43.6 (d), 47.93 (s, C13), 50.38 (d), 114.94 (d, C-4), 135.04 (d, C-1), 128.84 (s), 130.92 (s), 139.02 (s), 152.7 (s, C-3) and 220 (s, C-17-C=O); MS m/z (FAB+) 502.1 [20, (M+NBA)$^+$], 349.1 [100, (M)$^+$], 271.0 (20); MS m/z (FAB−) 502.2 [40, (M+NBA)$^-$], 348.1 [100, (M−H)$^-$]; Acc. MS (FAB+) 348.07532 C$_{18}$H$_{21}$BrO$_2$ requires 348.07249. Found C, 60.72; H, 5.94. C$_{18}$H$_{21}$BrO$_2$ requires C, 61.9; H, 6.06%.

2-Bromooestrone 3-O-sulphamate (4)

Upon sulphamoylation, 3 (500 mg, 1.431 mmol) gave a crude product (620 mg) which was fractionated by flash chromatography (chloroform/acetone, 8:1). The beige residue obtained (510 mg) was further purified by recrystallization from acetone/hexane (1:2) to give 3 as beige crystals (405 mg, 66%) mp>155° C. (dec.); TLC (chloroform/acetone, 8:1 and 4:1): Rfs 0.43 and 0.61 respectively; νmax (KBr) 3500, 3300 (NH$_2$), 1730 (C=O), 1390 (SO$_2$N) cm$^{-1}$; $\delta_H$(400 MHz, acetone-d$_6$) 0.92 (3H, s, C$\underline{H}_3$), 1.41–2.49 (13H, m), 2.86 (2H, m, C-6-$\underline{H}_2$), 7.27 (1H, s, C-4-$\underline{H}$), 7.32 (2H, br s, exchanged with D$_2$O, OSO$_2$N$\underline{H}_2$) and 7.55 (1H, s, C-1-$\underline{H}$); MS m/z (FAB+) 428.1 [100, (M)$^+$], 349.2 [40, (M+H−SO$_2$NH$_2$)$^+$]; MS m/z (FAB−) 580.2 [M−H+NBA], 428.1 [100, (M)$^-$], 349.1 [30, (M+H−SO$_2$NH$_2$)$^-$]; Acc. MS (FAB+) 428.04299 C$_{18}$H$_{23}$BrNO$_4$S requires 428.05311. Found, C, 49.1; H 5.18; N, 3.60; C$_{18}$H$_{22}$BrNO$_4$S requires C, 50.47; H, 5.18; N, 3.27%.

2-Iodooestrone Acetate (5)

This was prepared from 1 (5.0 g, 16.01 mmol) in the same manner as the preparation of 2 except that copper iodide (18.29 g, 96.03 mmol) was used. The crude product obtained was purified by flash chromatography with ethyl acetate/hexane (1:4), and the yellow solid obtained (6.25 g) was further purified by recrystallization from methanol to give 5 as pale yellow crystals (5.89 g, 84%); mp 170–172° C. (crystals turned brown at >145° C.); TLC (chloroform/acetone, 8:1 and ethyl acetate, 4:1): Rfs 0.8 and 0.67 respectively; νmax (KBr) 1770, 1730 (C=O), $\delta_H$(400 MHz, CDCl$_3$) 0.92 (3H, s, C-18-C$\underline{H}_3$), 1.4–2.31 (12H, m), 2.34 (3H, s, C$\underline{H}_3$CO), 2.5 (1H, m), 2.87 (2H, t, J=4.27 Hz, C-6-C$\underline{H}_2$), 6.82 (1H, s C-4-$\underline{H}$) and 7.69 (1H, s, C-1-$\underline{H}$); MS m/z (FAB+) 592.1 [20, (M+H+NBA)$^+$], 439.1 [80, (M+H)$^+$], 396.1 [100, (M+H−CH$_3$CO)$^+$], 270.2 (40); Acc. MS (FAB+) 439.07667 C$_{20}$H$_{24}$IO$_3$ requires 439.07702. Found C, 54.2; H, 5.3 C$_{20}$H$_{23}$IO$_3$ requires C, 54.81; H, 5.29%.

2-Iodoestrone (6)

This was prepared from 5 (4.0 g, 9.126 mmol) in the same manner as the preparation of its bromo analogue 3. The yellow crude product obtained was recrystallized from mthanol to give 6 as pale yellow crystals (3.29 g, 91%); mp 207–209° C. (crystals turned brown at >169° C.); TLC (chloroform/acetone, 8:1): Rf 0.75; νmax (KBr) 3400 (OH), 1730 (C=O) cm$^{-1}$; $\delta_H$(270 MHz, CDCl$_3$) 0.91 (3H, s, C-18-C$\underline{H}_3$), 1.4–2.56 (13H,m), 2.83 (2H, m, C-6-C$\underline{H}_2$), 5.24 (1H, s, exchanged with D$_2$O, C-3-O$\underline{H}$), 6.74 (1H, s, C-4-$\underline{H}$) and 7.52 (1H, s, C-1-$\underline{H}$); $\delta_C$ (400 MHz, CDCl$_3$) 13.82 (q, C-18), 21.57 (t), 25.89 (t), 26.26 (t), 29.98 (t), 31.57 (t), 31.81 (t), 39.0 (d), 43.9 (d), 48.3 (s, C13), 50.38 (d), 116.54 (d, C-4), 138.14 (d, C-1), 129.64 (s), 131.92 (s), 138.02 (s), 153.6 (s, C-3) and 220 (s, C-17, C=O); MS m/z (FAB+) 550.1 [20, (M+H+NBA)$^+$], 396.1 [100, (M)$^+$], 271.2 (40);

MS m/z (FAB−) 549.2 [20, (M+NBA)+], 395.1 [100, (M−H)−]; Acc. MS (FAB+) 397.0651 $C_{18}H_{22}IO_2$ requires 397.06646. Found C, 53.7; H, 5.34; $C_{18}H_{21}IO_2$ requires C, 54.56; H, 5.34%.

2-Iodooestrone 3-O-sulphamate (7)

Upon sulphamoylation, 6 (500 mg, 1.262 mmol) gave a crude product which was fractionated by flash chromatography (chloroform/acetone, 8:1). The beige residue that obtained (450 mg) was further purified by recrystallization from acetone/hexane (1:2) to give 7 as beige crystals (342 mg, 57%); mp>145° C. (dec.); TLC (chloroform/acetone, 8:1 and 4:1): Rfs 0.61 and 0.73 respectively; vmax (KBr) 3500, 3200 ($NH_2$), 1720 (C=O), 1390 ($SO_2$) cm$^{-1}$; $\delta_H$ (400 MHz, acetone-$d_6$) 0.92 (3H, s, $CH_3$), 1.4–2.53 (13H, m), 2.83 (2H, m, C-6-$H_2$), 7.25 (1H, s, C-4-$H$), 7.32 (2H, br s, exchanged with $D_2O$, $OSO_2NH_2$) and 7.76 (1H, s, C-1-$H$); MS m/z (FAB+) 629.1 [40, (M+H+NBA)+], 476.1 [100, (M+H)+], 396.1 [40, (M+H−$SO_2NH_2$)+]; MS m/z (FAB−) 628.1 [35, (M+NBA)−], 474.1 [100, (M−H)−], 395.1 [20, (M−$SO_2NH_2$)−]; Acc. MS (FAB+) 476.03874 $C_{18}H_{23}INO_4S$ requires 476.03926. Found, C, 45.8; H, 4.74; N, 2.85; $C_{18}H_{22}INO_4S$ requires C, 45.48; H, 4.66; N 2.95%.

The title compound—which is pictorially presented in FIG. 7—is sometimes referred to as "2-IodoEMATE". Results for this compound are presented in FIGS. 8 and 9.

2-Chloroestrone Acetate (8)

This was prepared from 1 (500 mg, 1.603 mmol) in the same manner as the preparation of 2 except that copper chloride (475 mg, 4.798 mmol) was used. The crude product obtained was purified by flash chromatography with ethyl acetate/hexane (1:4), and the pale yellow solid obtained (526 mg) was further purified by recrystallization from methanol to give 8 as white crystals (436 mg, 78%); mp 195–197° C.; TLC (chloroform/acetone, 8:1 and ethyl acetate, 4:1): Rfs 0.78 and 0.67 respectively; vmax (KBr) 1770, 1730 (C=O), $\delta_H$(400 MHz, $CDCl_3$) 0.90 (3H, s, C-18-$CH_3$), 1.38–2.29 (12H, m), 2.33 (3H, s, $CH_3CO$), 2.5 (1H, m), 2.87 (2H, m, C-6-$CH_2$), 6.85 (1H, s, C-4-$H$) and 7.34 (1H, s, C-1-$H$).

2-Chloroestrone (9)

This was prepared from 8 (400 mg, 1.15 mmol) in the same manner as the preparation of its bromo analogue 3. The pale yellow crude product obtained was recrystallized from methanol to give 9 as white crystals (320 mg, 90%); mp 221–223° C.; TLC (chloroform/acetone, 8:1): Rf 0.70; vmax (KBr) 3400 (OH), 1730 (C=O) cm$^{-1}$; $\delta_H$ (270 MHz, $CDCl_3$) 0.91 (3H, s, C-18-$CH_3$), 1.4–2.54 (13H, m), 2.84 (2H, m, C-6-$CH_2$), 5.27 (1H, s, exchanged with $D_2O$, C-3-O $H$), 6.71 (1H, s, C4-$H$) and 7.31 (1H, s, C-1-$H$).

2-Chloroestrone 3-O-sulphamate (10)

Upon sulphamoylation, 6 (200 mg, 655 μmol) gave a crude product which was fractionated by flash chromatography (chloroform/acetone, 8:1). The beige residue that obtained (190 mg) was further purified by recrystallization from acetone/hexane (1:2) to give 10 as white crystals (170 mg, 68%); mp>163° C. (dec.); TLC (chloroform/acetone, 8:1 and 4:1): Rfs 0.63 and 0.74 respectively; vmax (KBr) 3500, 3200 ($NH_2$), 1720 (C=O), 1390($SO_2$) cm$^{-1}$; $\delta_H$(400 MHz, $CDCl_3$/DMSO-$d_6$; 10:1) 0.93 (3H, s, $CH_3$), 1.4–2.51 (13H, m), 2.86 (2H, m, C-6-$H_2$), 7.01 (2H, br s, exchanged with $D_2O$, $OSO_2NH_2$), 7.25 (1H, s, C-4-$H$) and 7.35 (1H, s, C-1-$H$).

2-Fluorooestrone Acetate (11)

Oestrone (1.50 g, 5.5 mmol) and N-fluoropyridinium triflate (2.74 g, 11.0 mmol) in 1,1,2-trichloroethane (24 ml) were refluxed under nitrogen for 24 hours. Solvent was removed under reduced pressure, and the residue poured into water and extracted with dichloromethane (3×100 ml), dried ($MgSO_4$), filtered and evaporated to give a crude brown oil which was dissolved in pyridine (10.5 ml) and treated with acetic anhydride (2.62 ml) under reflux for two hours. The solvent was evaporated and the residue poured into ice-water. The solution was extracted with dichloromethane (3×100 ml) dried ($MgSO_4$), filtered and evaporated to give a crude solid. Purification by flash-column chromatography using petroleum ether (b.p. 60–80° C.): ethyl acetate (9:1 to 7:3) as eluent afforded 0.85 g of a crude mixture after evaporation. Recrystallization from petroleum ether (b.p. 60–80° C.): absolute ethanol (2:8) gave as first crop the 2-fluorooestrone acetate 11 predominantly (purity 75–80% estimated by $^1$HNMR) (215 mg, 12% yield) as colourless crystals.

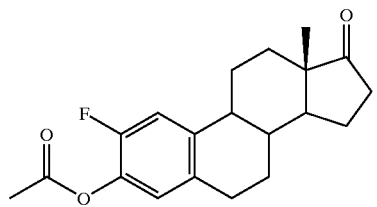

Ref. See P. C. Bulman Page, F. Hussain, J. L. Maggs, P. Morgan and B. Kevin Park, *Tetrahedron*, 46, 2059–2068, 1990.

$C_{20}H_{23}FO_3$
MW 330.39
Mp ° C. 83–88 (litt. 88–90)
$^1$H NMR 270 MHz ($CDCl_3$): 0.91 (s, 3H, C-18-$CH_3$), 1.38–1.75 (m, 6H), 1.90–2.45 (m, 6H), 2.32 (s, 3H, $CH_3$) 2.46–2.57 (m, 1H), 2.80–2.95 (m, 2H, C-6-H), 6.83 (d, 1H, J=8.3 Hz, C-4-H), 7.07 (d, 1H, J=13.2 Hz, C-1-H).
M/S m/z (+ve FAB, rel. int.): 331.1 (59, M+ +1), 288.1 (100), 270.1 (22).
HRMS (+ve FAB) m/z calcd for $C_{20}H_{23}FO_3$ (M+ +1) 331.170948, found 331.170464.

2-Fluorooestrone (12)

2-Fluorooestrone acetate 11 (185 mg, 0.56 mmol) was dissolved in methanol (5 ml) and deacetylated by heating with $K_2CO_3$ (387 mg, 5 equiv.) under reflux for 3 hours. After evaporation of the solvent, water (25 ml) was added and the product extracted by dichloromethane (3×20 ml). The extract was dried over $MgSO_4$, evaporated under reduce pressure. Recrystallisation from petroleum ether (b.p. 60–80° C.): absolute ethanol (2:8) gave 2-fluorooestrone (121 mg, purity estimated by $^1$H NMR 75%) as colourless crystal (m.p. 220–227° C.). Further purification by HPLC preparative, solvent MeOH:$H_2O$=60:40, flow 20 ml/min, Column Waters Radialpak C18 100×25 mm, detection 254 & 270 nm gave, after evaporation of the solvents, 2-fluorooestrone 12 as a white solid (72 mg, 45% yield).

Ref. See P. C. Bulman Page et al., *Tetrahedron*, 46, 2059–2068, 1990.

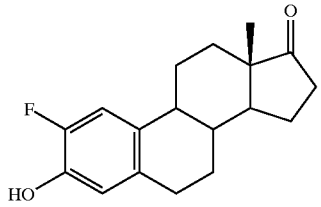

$C_{18}H_{21}FO_2$
MW 288.36

Mp ° C. 220–223 [Litt. 220–222 (petroleum ether-absolute ethanol)]

$^1$H NMR 400 MHz (CDCl$_3$): 0.78 (s, 3H, C-18-C$\underline{H}$$_3$), 1.37–1.79 (m, 6H), 1.91–2.40 (m, 6H), 2.46–2.56 (m, 1H), 2.80–2.90 (m, 2H, C-6-H), 5.02 (d, 1H exch. D$_2$O, J=3.9 Hz, —O$\underline{H}$), 6.72 (d, 1H, J=9.4 Hz, C-4-H), 6.98 (d, 1H, J=12.5 Hz, C-1-H).

$^{19}$F NMR 376 MHz (CDCl$_3$): −144.50 (t, 1F, J=9.2 Hz).

HPLC Waters: eluent MeOH:H$_2$O=60:40, flow 2 ml/min, Column Waters Radialpak C18 8×100 mm, detection 270 nm, 2-fluorooestrone RT=11.69 min 96.85%, impurity RT=9.69 min, 3.15%.

M/S m/z (+ve FAB, rel. int.): 289.0 [100, (M$^+$+1)], 149.0 (33), 120.0 (35).

M/S m/z (−ve FAB, rel. int.): 287.1.0 [100, (M$^−$−1)], 200.0 (25), 140.0 (25), 123.0 (43).

HRMS (+ve FAB) m/z calcd for C$_{18}$H$_{21}$FO$_2$, M$^+$288.152558, found 288.151993.

2-Fluorooestrone-3-O-sulphamate (13)

To a stirred solution of 2-fluorooestrone 12 (65 mg, 0.23 mmol) in anhydrous DMF (7 ml) under an atmosphere of nitrogen was added at room temperature DMBP (139 mg, 0.68 mmol) then a solution of sulphamoyl chloride 0.68 M in toluene (1.61 ml, 1.13 mmol) via syringe. The reaction mixture was stirred at room temperature for 18 hours. Water (50 ml) and ethyl acetate (60 ml) were added and upon separation, the organic layer was washed with brine (3×50 ml). The organic layer was dried over magnesium sulfate, filtered and evaporated under reduced pressure. The obtained crude product was purified by flash chromatography (column ∅=2.5 cm, h=20 cm) using as eluent chloroform:acetone=8:1 to afford 2-fluorooestrone-3-O-sulphamate 13 as a white solid, (47 mg, 57% yield).

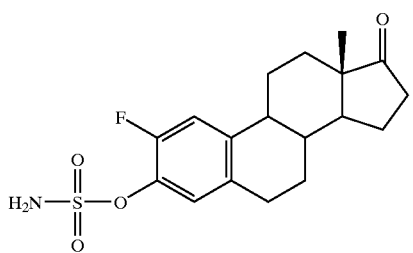

C$_{18}$H$_{22}$NO$_4$FS
MW 367.44
Mp 189–193° C.

$^1$H NMR 400 MHz (CDCl$_3$): 0.91 (s, 3H, C-18-C$\underline{H}$$_3$), 1.36–1.70 (m, 6H), 19.2–2.36 (m, 6H), 2.46–2.57 (m, 1H), 2.80–2.95 (m, 2H, C-6-H), 5.03 (s broad, 2H exch. D$_2$O, —N$\underline{H}$$_2$), 7.11 (d, 1H, J=9.7 Hz, C-4-H), 7.13 (d, 1H, J=15.5 Hz, C-1-H).

$^{19}$F NMR 376 MHz (CDCl$_3$): −113.24 (dd, 1F, J=15.5 Hz and J=9.7 Hz)

MS m/z (+ve FAB, rel. int.): 367.0 (100, M$^+$), 350.0 (30), 288.1 (49), 258.0 (32), 243.1 (38), 178 (34), 133.0 (30), 97.0 (35).

M/S m/z (−ve FAB, rel. int.): 366.0 [100, (M−H)$^−$], 77.9 (21).

HRMS (+ve FAB) m/z calcd for C$_{18}$H$_{22}$NO$_4$S M$^+$367.125358, found 367.126663 Rf 0.32 (CHCl$_3$:acetone=8:1), SM Rf 0.58

Inhibition of Oestrone Sulphatase Activity by Halo-EMATEs in Placental Microsomes A sulphatase—positive human placenta was used as a source of placental microsomes. Tissue was homogenised and nuclei and cell debris removed by centrifugation at 2000×g for 30 min. Placental microsomes were obtained by centrifugation of the resulting supernatant at 100,000×g for 1 h.

For inhibition studies placental microsomes (125 μg/ml) were incubated in the absence or presence of inhibitors (1 pm–1.0 μM) with $^3$H estrone sulphate (E1S, 2×10$^5$ dpm adjusted to 20 μM with unlabelled E1S for 60 mins. [4-$^{14}$C E1] (7×10$^3$ dpm) was added to correct for procedural losses and free and sulphated steroids separated by solvent partition using toluene. A portion of the solvent was removed and the $^3$H and $^{14}$C content determined by liquid scintillation spectrometry.

The data obtained are represented in FIG. 13.

Further data are given in the table below.

| Compound | Plate Assay in MCF −7 cells % Inhibition at 10 μM |
|---|---|
| 2-Cl-Emate | 35 |
| 2-Br-Emate | 33 |
| 2-I-Emate | 25 |

Effect of Halo-EMATES on T47D Cell Growth (Plate Assay)

T47D receptor positive breast cancer cells were seeded into a 96 well cell culture plate and allowed to grow until approximately 70% confluent. Cells were treated with either vehicle (controls, tetrahydrofuran in medium) or halo-EMATEs (1 or 10 μM) and cultured for a further 24 h. At the end of this period effects of the drugs on cell numbers were determined using a microtitre plate assay (Cell Titre 96 cell proliferation assay, Promega). In this assay the conversion of substrate by untreated cells at the end of the culture period was set at 100%.

The data obtained are represented in FIG. 14.

Further data are given in the table below.

| | Cell assay of T47D cells | | |
|---|---|---|---|
| Compound | % Inhibition at 1 μM | % Inhibition at 10 μM | Morphology |
| 2-F-Emate | <1 | 30 | + |
| 2-Cl-Emate | 1 | 7.5 | + |
| 2-Br-Emate | − | − | + |
| 2-I-Emate | − | − | + |

+ has effect on cell morphology

All publications and patents mentioned in the above specification are herein incorporated by reference.

Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims.

What is claimed is:
1. A compound selected from the group consisting of:

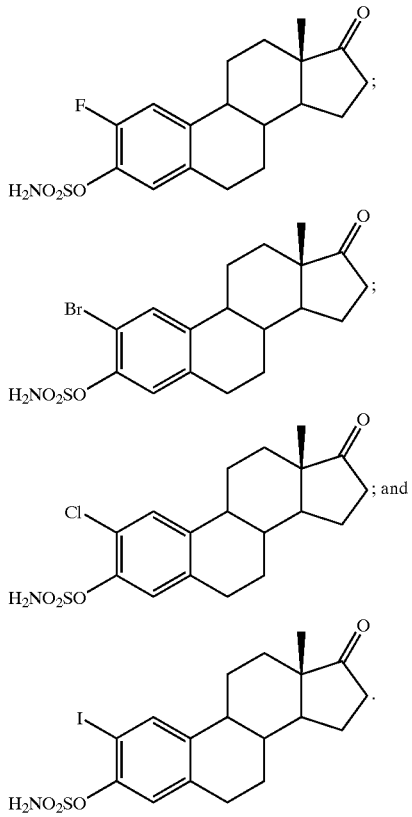

2. A compound of the formula

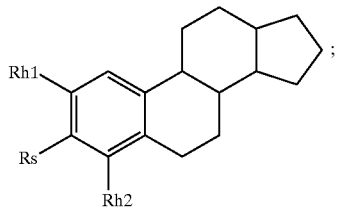

wherein
Rh1 is an optional halo group;
Rh2 is an optional halo group;
at least one of Rh1 and Rh2 is present;
Rs is a sulphamate group; and
wherein said compound inhibits steroid sulphatase (STS) activity.

3. The compound according to claim 2 having the formula

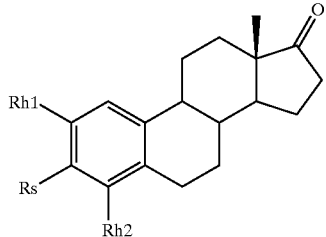

wherein Rh1, Rh2 and Rs are as defined in claim 2.

4. The compound according to claim 2 wherein Rs has the formula

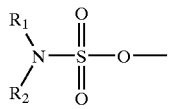

wherein $R_1$ and $R_2$ are independently selected from H, alkyl, cycloalkyl, alkenyl and aryl, or combinations thereof, or together represent alkylene, wherein the or each alkyl or cycloalkyl or alkenyl optionally contain one or more hetero atoms or groups.

5. The compound according to claim 4 wherein at least one of $R_1$ and $R_2$ is H.

6. The compound according to claim 4 wherein each of $R_1$ and $R_2$ is H.

7. A compound of the formula

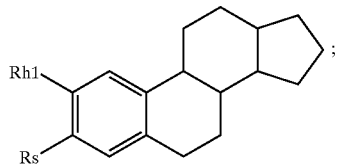

wherein
Rh1 is a halo group;
Rs is a sulphamate group; and
wherein said compound inhibits steroid sulphatase (STS) activity.

8. The compound according to claim 7 having the formula

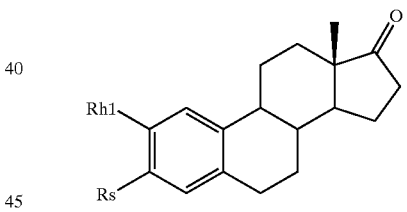

wherein Rh1 and Rs are as defined in claim 7.

9. The compound according to claim 7 wherein Rs has the formula

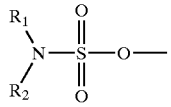

wherein $R_1$ and $R_2$ are independently selected from H, alkyl, cycloalkyl, alkenyl and aryl, or combinations thereof, or together represent alkylene, wherein the or each alkyl or cycloalkyl or alkenyl optionally contain one or more hetero atoms or groups.

10. The compound according to claim 9 wherein at least one of $R_1$ and $R_2$ is H.

11. The compound according to claim 9 wherein each of $R_1$ and $R_2$ is H.

12. The compound according to claim 8 wherein Rs has the formula

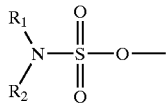

wherein $R_1$ and $R_2$ are independently selected from H, alkyl, cycloalkyl, alkenyl and aryl, or combinations thereof, or together represent alkylene, wherein the or each alkyl or cycloalkyl or alkenyl optionally contain one or more hetero atoms or groups.

13. The compound according to claim 12 wherein at least one of $R_1$ and $R_2$ is H.

14. The compound according to claim 12 wherein each of $R_1$ and $R_2$ is H.

15. The compound according to claim 9 wherein Rh1 is fluorine group.

16. The compound according to claim 9 wherein Rh1 is bromine group.

17. The compound according to claim 9 wherein Rh1 is chlorine group.

18. The compound according to claim 9 wherein Rh1 is iodine group.

19. The compound according to claim 12 wherein Rh1 is fluorine group.

20. The compound according to claim 12 wherein Rh1 is bromine group.

21. The compound according to claim 12 wherein Rh1 is chlorine group.

22. The compound according to claim 12 wherein Rh1 is iodine group.

23. A pharmaceutical composition comprising the compound according to claim 2 optionally admixed with a pharmaceutically acceptable carrier, diluent, excipient or adjuvant.

24. A method of manufacturing a medicament to inhibit STS activity or of a therapy for a condition or disease associated with STS comprising admixing the compound according to claim 2 with a pharmaceutically acceptable carrier, diluent, excipient or adjuvant.

25. A method for inhibiting STS activity in a subject in need thereof or of a therapy for a condition or disease associated with adverse STS levels in a subject in need thereof comprising administering to a subject in need thereof an effective amount of the compound according to claim 2.

* * * * *